United States Patent
Baguisi et al.

(10) Patent No.: US 9,540,417 B2
(45) Date of Patent: *Jan. 10, 2017

(54) COMPOSITIONS AND METHODS FOR TREATING ISCHEMIA AND ISCHEMIA-REPERFUSION INJURY

(71) Applicant: Ischemix LLC, Maynard, MA (US)

(72) Inventors: Alexander Baguisi, Grafton, MA (US); Reinier Beeuwkes, Concord, MA (US); Ralph Casale, Westford, MA (US); Steven A. Kates, Needham, MA (US); Alan S. Lader, Stoughton, MA (US)

(73) Assignee: Ischemix LLC, Maynard, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/918,175

(22) Filed: Oct. 20, 2015

(65) Prior Publication Data

US 2016/0264622 A1  Sep. 15, 2016

Related U.S. Application Data

(63) Continuation of application No. 14/283,844, filed on May 21, 2014, now abandoned, which is a continuation of application No. 13/041,001, filed on Mar. 4, 2011, now Pat. No. 8,772,249, which is a continuation of application No. 12/466,170, filed on May 14, 2009, now Pat. No. 7,928,067.

(51) Int. Cl.
| | |
|---|---|
| C07K 5/072 | (2006.01) |
| A61K 31/385 | (2006.01) |
| A61K 47/48 | (2006.01) |
| A61K 31/381 | (2006.01) |
| A61K 38/05 | (2006.01) |
| A61K 38/00 | (2006.01) |

(52) U.S. Cl.
CPC ......... *C07K 5/06104* (2013.01); *A61K 31/381* (2013.01); *A61K 31/385* (2013.01); *A61K 38/05* (2013.01); *A61K 47/48246* (2013.01); *A61K 38/00* (2013.01)

(58) Field of Classification Search
CPC .... A61K 38/05; A61K 31/381; A61K 31/385; C07K 5/06104
See application file for complete search history.

(56) References Cited

U.S. PATENT DOCUMENTS

| | | |
|---|---|---|
| 3,875,207 A | 4/1975 | Iselin et al. |
| 5,288,706 A | 2/1994 | Yamanouchi et al. |
| 5,318,987 A | 6/1994 | Wieithmann et al. |
| 5,455,264 A | 10/1995 | Beisswenger et al. |
| 6,013,663 A | 1/2000 | Fujita et al. |
| 6,127,339 A | 10/2000 | Hatanaka et al. |
| 6,271,254 B1 | 8/2001 | Ulrich et al. |
| 6,348,490 B1 | 2/2002 | Hettch et al. |
| 6,441,024 B1 | 8/2002 | Klatt et al. |
| 6,544,718 B2 | 4/2003 | Goto |
| 6,890,896 B1 | 5/2005 | Shashoua |
| 7,030,154 B2 | 4/2006 | Ames |
| 7,202,270 B2 | 4/2007 | Majeed et al. |
| 7,524,819 B2 | 4/2009 | Shashoua |
| 7,928,067 B2 * | 4/2011 | Baguisi ............... A61K 31/385 514/16.4 |
| 8,410,162 B2 | 4/2013 | Garner et al. |
| 8,772,249 B2 * | 7/2014 | Baguisi ............... A61K 31/385 514/21.91 |
| 8,772,250 B2 * | 7/2014 | Baguisi ............... A61K 31/385 514/21.91 |
| 8,815,937 B2 | 8/2014 | Baguisi et al. |
| 9,359,325 B2 | 6/2016 | Baguisi et al. |
| 2002/0035243 A1 | 3/2002 | Imfeld et al. |
| 2002/0048798 A1 | 4/2002 | Avery et al. |
| 2004/0204340 A1 | 10/2004 | Hamilton et al. |
| 2005/0153291 A1 | 7/2005 | Harwich et al. |
| 2006/0019901 A1 | 1/2006 | Shashoua |

(Continued)

FOREIGN PATENT DOCUMENTS

| | | |
|---|---|---|
| CA | 2582027 | 9/2007 |
| DE | 10 47 991 B | 12/1958 |

(Continued)

OTHER PUBLICATIONS

1995 Sigma Peptides and Amino Acids Catalog, cover page, pp. 1, 143-144.

Adger, B., et al., "The Synthesis of (R)-(+)-Lipoic Acid Using a Monooxygenase-Catalysed Biotransformation as the Key Step," Bioorganic and Mechanical Chemistry, 5(2): 253-261 (1997).

Anderson, MD, Cancer Center News Release Dated Feb. 25, 2010, "New Strategy Develops Two Prototype Drugs Against Cancer, Retinal Diseases," Retrieved from internet on Dec. 1, 2010: http://www.mdanderson.org/newsroom/news-releases/2010/new-strategy-develops-two-pr . . . , 4 pages.

(Continued)

*Primary Examiner* — Christina Bradley
(74) *Attorney, Agent, or Firm* — Hamilton, Brook, Smith & Reynolds, P.C.

(57) ABSTRACT

The present invention relates to compositions comprising a substantially pure compound represented by Structural Formula I:

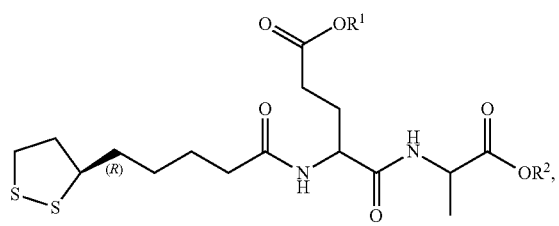

and methods of using such compounds to activate cytoprotective kinases. The values and preferred values of the variables in Structural Formula I are defined herein.

14 Claims, 7 Drawing Sheets

(56) References Cited

U.S. PATENT DOCUMENTS

| | | |
|---|---|---|
| 2007/0287195 A1 | 12/2007 | Suda |
| 2009/0082281 A1 | 3/2009 | Shashoua |
| 2009/0306190 A1 | 12/2009 | Stenzel-Poore et al. |
| 2010/0292313 A1 | 11/2010 | Baguisi et al. |
| 2010/0317873 A1 | 12/2010 | Chiu |
| 2011/0160294 A1 | 6/2011 | Baguisi et al. |
| 2012/0135932 A1 | 5/2012 | Baguisi et al. |
| 2013/0237483 A1 | 9/2013 | Baguisi et al. |
| 2014/0274917 A1 | 9/2014 | Baguisi et al. |
| 2015/0065564 A1 | 3/2015 | Baguisi et al. |
| 2015/0329519 A1 | 11/2015 | Kates et al. |

FOREIGN PATENT DOCUMENTS

| | | |
|---|---|---|
| EP | 0 063 879 | 11/1989 |
| EP | 0424282 | 4/1991 |
| EP | 0 869 126 | 7/2002 |
| EP | 1 371 640 | 12/2003 |
| EP | 1 454 627 | 9/2004 |
| JP | 9-90542 | 4/1997 |
| JP | 11-7099 | 1/1999 |
| JP | 2000 169371 | 6/2000 |
| JP | 2003 048833 | 2/2003 |
| JP | 2003-518477 | 6/2003 |
| JP | 2003-286168 | 10/2003 |
| JP | 2004-51624 | 2/2004 |
| JP | 2006-22066 | 1/2006 |
| JP | 2007 070303 A | 3/2007 |
| NZ | 596364 | 10/2013 |
| WO | WO 93/22320 | 11/1993 |
| WO | WO 97/18235 | 5/1997 |
| WO | WO 99/45922 | 9/1999 |
| WO | WO 01/09118 | 2/2001 |
| WO | WO 01/36454 | 5/2001 |
| WO | WO 02/096360 | 12/2002 |
| WO | WO 03/055853 | 7/2003 |
| WO | WO 03/070714 | 8/2003 |
| WO | WO 03/072052 | 9/2003 |
| WO | WO 2004/004632 | 1/2004 |
| WO | WO 2005/063732 | 7/2005 |
| WO | WO 2006/101909 | 9/2006 |
| WO | WO 2006/117995 A1 | 11/2006 |
| WO | WO 2007/027559 | 3/2007 |
| WO | WO 2010/052310 A1 | 5/2010 |
| WO | WO 2006/101910 | 9/2010 |
| WO | WO 2010/132657 | 11/2010 |
| WO | WO 2010/147957 | 12/2010 |
| WO | WO 2011/080725 | 7/2011 |
| WO | WO 2012/067947 | 5/2012 |
| WO | WO 2015/174948 A1 | 11/2015 |

OTHER PUBLICATIONS

Bala, M., et al., "Novel Peptidominics as Angiotensin-Converting Enzyme Inhibitors: A Combinatorial Approach," Bioorganic and Medicinal Chemistry, 10(11): 3685-3691 (Nov. 2002).
Bartzatt, R.L., "Utilizing a D-Amino Acid as a Drug Carrier for Antineoplastic Nitrogen Mustard Groups," Drug Delivery, 12(3): 141-147 (2005), abstract only.
Bastin, R.J., et al., "Salt Selection and Optimisation Procedures for Pharmaceutical New Chemical Entities," Organic Process Res. and Dev., 427-435 (2000).
Berg, T., et al. Biochemistry Fifth Edition, pp. 43, 467 and 468 (2001).
Bessalle, R. et al., "All-D-magainin: Chirality, Antimicrobial Activity and Proteolytic Resistance," FEBS Lett., 274(1, 2): 151-155 (Nov. 1990).
Biewenga, G., et al., "The Pharmacology of the Antioxidant Lipoic Acid," Gen. Pharmac., 29(3): 315-331 (1997).
Bilska, A., et al., "Lipoic Acid—the Drug of the Future," Pharmacological Reports, 57(5): 570-577 (Jan. 2005).
Branden, C. and J. Tooze, Introduction to Protein Structure 2nd. Ed. pp. 4-5 (1999).
Bunjes, N., et al., "Thiopeptide-Supported Lipid Layers on Solid Substrates," Langmuir, 13:6188-6194 (1997).
CAPLUS Accession No. 2006-1007709, CAS abstract for Kates WO 2006101909, published 2006.
CAPLUS Accession No. 2008: 1371872, published 2008.
CAS display of compounds in WO 2006/101909, published Sep. 28, 2006 and entitled "Combination Therapy for Treating and Preventing Diseases."
Chemical Abstract Service Job Listing for Scientific Information Analysis, Retrieved from internet on Oct. 20, 2010: https://jobs.cas.org/epostings/submit.cfm?fuseaction=app.jobinfo&jobid=205158&compa.
Chemical Abstract Service, Job Listing for Part-Time Organic Chemistry, Retrieved from internet on Oct. 20, 2010: https://jobs.cas.org/epostings/submit.cfm?fuseaction=app.jobinfo&id=23&jobid=205101.
Clever Approach May Provide New Clues to Drug Design, Retrieved from Internet on Dec. 9, 2010: http://www.wi.mit.edu/scripts/pfl.php?p=http:/www.wi.mit.edu/news/archives/1996/pk_0 . . . , 2 pages.
"The Polymeric Nature of Proteins", In Proteins: Structures and Molecular Properties, 2nd Edition, Creighton, T.E. ed. (NY: W.H. Freeman and Company) p. 2 (1984).
Development and Uses of Alitame: A Novel Dipeptide Amide Sweetener, Glowaky, R.C. et al., Abstract only, Retrieved from Internet on Nov. 19, 2010: http://pubs.acs.org/doi/abs/10.1021/bk-1991-0450.ch005.
Fields, G.B. and R.L. Noble, "Solid Phase Peptide Synthesis Utilizing 9-Fluorenylmethosycarbonyl Amino Acids," Int. J. Peptide Protein Res. 35: 161-214 (1990).
Hagen, T.M., et al., "(R)-alpha-Lipoic Acid Reverses the Age-Associasted Increase in Susceptibility of Hepatocytes to tert-Butylhydroperoxide Both In Vitro and In Vivo," Antioxidants and Redox Signaling, 2(3): 473-486 (2000).
Hardesty, J.O., et al., "Enzymatic Proteolysis of a Surface-Bound α-Helical Polypeptide," Langmuir 24: 13944-13956 (2008).
Holmquist, L., et al., "Lipoic Acid as a Novel Treatment for Alzheimer's Disease and Related Dementias," Pharmacology and Therapeutics, 113: 154-164 (2007).
Jia, L., et al., "Protective Effect of Lipoic Acid Against Acrolein-Induced Cytotoxicity in IMR-90 Human Fibroblasts," J. Nutr. Sci. Vitaminol., 55: 126-130 (2009).
Kates, S., et al., "Lipoic acid analogs with enhanced pharmacological activity," Bioorganic & Medicinal Chemistry 22(1):505-512 (2014).
Khoronenkova, S.V. and Tishkov, V.I., "D-Amino Oxidase: Physiological Role and Applications", Biochemistry, 73(13):1511-1518 (2008).
Kilic, F., et al., "Modelling Cortical Cataractogenesis XX. In Vitro Effect of Alpha-Lipoic Acid on Glutathione Concentrations in Lens in Model Diabetic Cataractogenesis," Biochemistry and Molecular Biology International, 46(3): 585-595 (Oct. 1998).
Metabolism of Nitrogen-Containing Compounds. Biochemistry, Zubay, p. 592, Table 24.2 (1998).
Nomenclature Policy: Abbreviated Designations of Amino Acids, Am. J. Clin. Nutr., 47, 581-588 (1988).
Nomenclature Policy: Abbreviated Designations of Amino Acids, Am. J. Clin. Nutr., 47, 589 (1988).
NovaBiochem. Catalog and Peptide Synthesis Handbook pp. x, xi, 1, 2, 18, 19 (1999).
Packer, L., et al., "Molecular Aspects of Lipoic Acid in the Prevention of Diabetes Complications," Nutrition, 17: 888-895 (2001).
Panigrahi, M., "[Alpha]-Lipoic Acid Protects Against Reperfusion Injury Following Cerebrial Ischemia in Rats," Brain Research, 717(1-2): 184-188 (Apr. 1996).
Pick, U., et al., "Glutathione Reductase and Lipoamide Dehydrogenase Have Opposite Stereospecficities for α-Lipoic Acid Enantiomers," Biochem. and Biophys. Res. Comm. 206(2): 724-730 (Jan. 1995).
Sato, et al., "Dihydroxyindole polymerization inhibitors, and their use for topical formulations inhibiting," STN International HCAPLUS database, Accession No. 2006:74266 (2006).

(56) References Cited

OTHER PUBLICATIONS

Sehirli, O., et al., "α-Lipoic Acid Protects Against Renal Ischaemia-Reperfusion Injury in Rats," Clin. Exp. Pharmacol. Phys., 35: 249-255 (2008).
Sela, M. and Zisman, E., "Different Roles of D-Amino Acids in Immune Phenomena," The FASEB Journal, 11: 449 (1997).
Smith, J.R., et al., "Differential Activity of Lipoic Acid Enantiomers in Cell Culture," Journal of Herbal Pharmacotherapy, 5(3): 43-54 (2005).
STN Tokyo, International, L-Alanine, N-[5-(3R)-1,2-dithiolan-3-yl-1-oxopentyl]-L-beta-glutamyl-, file Registry [online], uploaded on Oct. 18, 2006, [searched on Jun. 6, 2013], CAS Registry No. 910627-26-8.
Van Der Meijden, M.W. et al., "Attrition-Enhanced Deracemization in the Synthesis of Clopidogrel—A Practical Application of a New Discovery," Organic Process Research and Development 13: 1195-1198 (2009).
Yu, G.L., et al., "Montelukast, a Cysteinyl Leukotriene Receptor-1 Antagonist, Dose- and Time-Dependently Protects against Focal Cerebral Ischemia in Mice," Pharmacology 73:31-40 (2005).
Wolz, P. and J. Krieglstein, "Neuroprotective Effects of α-Lipoic Acid and Its Enantiomers Demonstrated in Rodent Models of Focal Cerebral Ischemia," Neuropharmacology, 35(3): 369-375 (1996).
Zimmer, G., et al., "Dose/Response Curves of Lipoic Acid R- and S-Forms in the Working Rat Heart During Reoxygenation: Superiority of the R-Enantiomer of Enhancement of Aortic Flow," J. Mol. Cell. Cardiol. 27: 1895-1903 (1995).
Zimmer, R., et al., "Enantioselective Synthesis of (S)- and (R)-6-Hydroxy-8-nonenecarboxylates by Asymmetric Catalysis: A Formal Synthesis of (R)-α-Lipoic Acid and Its (S)-Antipode," Tetrahedron: Asymmetry, 11:879-887 (2000).
Office Action for U.S. Appl. No. 12/466,170, "Compositions and Methods for Treating Ischemia and Ischemia-Reperfusion Injury", date of mailing Jul. 22, 2009.
Final Office Action for U.S. Appl. No. 12/466,170, "Compositions and Methods for Treating Ischemia and Ischemia-Reperfusion Injury", date of mailing Nov. 12, 2009.
Final Office Action for U.S. Appl. No. 12/466,170, "Compositions and Methods for Treating Ischemia and Ischemia-Reperfusion Injury", date of mailing Oct. 23, 2009.
Notice of Allowance for U.S. Appl. No. 12/466,170, "Compositions and Methods for Treating Ischemia and Ischemia-Reperfusion Injury", date of mailing Mar. 2, 2011.
Interview Summary dated Oct. 16, 2009 for U.S. Appl. No. 12/466,170, "Compositions and Methods for Treating Ischemia and Ischemia-Reperfusion Injury", date of mailing Oct. 16, 2009.
Interview Summary for U.S. Appl. No. 12/466,170, "Compositions and Methods for Treating Ischemia and Ischemia-Reperfusion Injury", date of mailing Oct. 19, 2009.
Interview Summary for U.S. Appl. No. 12/466,170, "Compositions and Methods for Treating Ischemia and Ischemia-Reperfusion Injury", date of mailing Sep. 17, 2009.
Office Action dated Nov. 4, 2013 for U.S. Appl. No. 13/041,001, entitled "Compositions and Methods for Treating Ischemia and Ischemia-Reperfusion Injury."
Office Action dated Nov. 1, 2013 for U.S. Appl. No. 13/319,839, entitled "Compositions and Methods for Treating Ischemia and Ischemia-Reperfusion Injury.".
International Preliminary Report on Patentability, PCT/US2010/034701, Date of Issuance: Nov. 15, 2011.
Notification of Transmittal of the International Search Report and the Written Opinion of the International Searching Authority dated Jul. 15, 2010 for Int'l Application No. PCT/US2010/034701 entitled "Compositions and Methods for Treating Ischemia and Ischemia-Reperfusion Injury."
International Search Report and Written Opinion, PCT/US2011/060259, "Lipoyl Compounds and Their Use for Treating Ischemic Injury", ; Date of Mailing: Jan. 27, 2012.
Notification Concerning Transmittal of International Preliminary Report on Patentability and Written Opinion, PCT/US2011/060259; "Lipoyl Compounds and Their Use for Treating Ischemic Injury", Date of Mailing: May 30, 2013.
EP 10720092.5, Communication dated Dec. 29, 2011, entitled "Compositions and Methods for Treating Ischemia and Ischemia-Reperfusion Injury."
EP 10720092.5, Intention to Grant dated Nov. 15, 2013, entitled "Compositions and Methods for Treating Ischemia and Ischemia-Reperfusion Injury."
Office Action dated Feb. 28, 2014 for U.S. Appl. No. 13/885,289, entitled "Lipyl Compounds and Their Use for Treating Ischemic Injury."
Notice of Allowance dated Mar. 10, 2014 for U.S. Appl. No. 13/319,839, entitled "Compositions and Methods for Treating Ischemia and Ischemia-Reperfusion Injury."
Notice of Allowance dated Feb. 25, 2014 for U.S. Appl. No. 13/041,001, entitled "Compositions and Methods for Treating Ischemia and Ischemia-Reperfusion Injury."
Notice of Allowance and Fee(s) Due, dated Jul. 14, 2014, for U.S. Appl. No. 13/885,289, entitled "Lipoyl Compounds and Their Use for Treating Ischemic Injury."
First Office Action dated Oct. 8, 2014 for CN Application No. 201180065214.1, entitled "Lipyl Compounds and Their Use for Treating Ischemic Injury."
Office Action dated Oct. 17, 2013 for U.S. Appl. No. 13/885,289, entitled "Lipoyl Compounds and Their Use for Treating Ischemic Injury."
International Search Report and Written Opinion for PCT/US2014/000090, "Compositions and Methods for Treating Ischemia and Ischemia-Reperfusion Injury", date of mailing Jul. 31, 2014.
Office Action , dated Apr. 21, 2015, for U.S. Appl. No. 14/283,844, entitled, "Compositions and Methods for Treating Ischemia and Ischemia-Reperfusion Injury".
Office Action for U.S. Appl. No. 14/456,646, "Lipoyl Compounds and Methods for Treating Ischemic Injury", date of mailing Jul. 21, 2015.
Written Opinion dated Aug. 5, 2014 for SG Application No. 2013036546, entitled "Lipyl Compounds and Their Use for Treating Ischemic Injury."
Second Written Opinion dated Jun. 23, 2015 for SG Application No. 2013036546, entitled "Lipyl Compounds and Their Use for Treating Ischemic Injury."
Barltrop, J.A., et al., "The Chemistry of 1,2-Dithiolane (Trimethylene Disulfide) as a Model for the Primary Quantum Conversion Act in Photosysthesis", JACS, 76:4348-4367 (1954).
Brown, P.R., "Effect of Solvent on the Photolysis of α-Lipoic Acid", JOC, 34:3131-3135 (1969).
Diesel, B., et al., Biochemistry 46: 2146-2155 (2007).
Guillonneau, C., et al., "Synthesis and pharmacological evaluation of new 1,2-dithiolane based antioxidants", *Eur. J. Med. Chem.*, 38:1-11 (2003).
International Search Report and Written Opinion, for PCT/US2014/000090, entitled "Compositions and Methods for Treating Ischemia and Ischemia-Reperfusion Injury", date of mailing Jul. 31, 2014.
Izutsu, K.-i., "Stabilization of Therapeutic Proteins by Chemical and Physical Methods" in Therapeutic Proteins Methods and Protocols, Molecular Biology 308, C.M. Smales, et al. eds. (NJ: Human Press), pp. 287-292 (2005).
Notice of Allowance for U.S. Appl. No. 14/456,646, "Lipoyl Compounds and Methods for Treating Ischemic Injury", date of mailing Mar. 16, 2016.
Office Action for U.S. Appl. No. 14/710,074, "Formulations Comprising Lipoyl Compounds", date of mailing Jul. 6, 2016.
Rosini, M., et al., Rational Approach to Discover Multipotent Anti-Alzheimer Drugs, J. Med. Chem, 48(20):360-363 (2005).
Thomas, R.C., et al., "Disulfide Polymers of DL-α-Lipoic Acid", *JACS*, 78:6148-6149 (1956).
Wagner, et al., "Properties and Derivatives of α-Lipoic Acid", *JACS*, 78:5079-5081 (1956).
Whiteman, M., et al., FEBS Letters 379: 74-76 (1996.

(56) References Cited

OTHER PUBLICATIONS

Ziegler, D., et al., "Treatment of symptomatic diabetic polyneuropathy with the antioxidant α-lipoic acid: a meta-analysis", *Diabetic Medicine*, 21:114-121 (2004).

* cited by examiner

COMPOSITIONS AND METHODS FOR TREATING ISCHEMIA AND ISCHEMIA-REPERFUSION INJURY

RELATED APPLICATIONS

This application is a continuation of U.S. application Ser. No. 14/283,844 filed May 21, 2014, which is a continuation of U.S. application Ser. No. 13/041,001, filed Mar. 4, 2011, now U.S. Pat. No. 8,772,249, issued Jul. 8, 2014, which is a continuation of U.S. application Ser. No. 12/466,170, filed May 14, 2009, now U.S. Pat. No. 7,928,067, issued Apr. 19, 2011.

The entire teachings of the above applications are incorporated herein by reference.

BACKGROUND OF THE INVENTION

In the United States, cardiovascular disease is the leading cause of death for both men and women. More than one million people suffer from heart attacks every year in the United States alone. Cardiac ischemia, a condition characterized by reduced blood flow and oxygen to the heart muscle, or myocardium, is one hallmark of cardiovascular disease that can ultimately lead to a heart attack, or myocardial infarction. Cardiovascular disease can also result in restricted blood flow and reduced oxygen supply to other areas of the body resulting in ischemic injuries to various organs and tissues, including the brain, which can lead to stroke.

Re-establishment of blood flow, or reperfusion, and re-oxygenation of the affected area following an ischemic episode is critical to limit irreversible damage. However, reperfusion also brings potentially damaging consequences, such as reperfusion injury, which is caused by the restoration of coronary blood flow after an ischemic episode and results from the generation and accumulation of reactive oxygen and nitrogen species during reperfusion. Ischemia-reperfusion injury is biochemically characterized by a depletion of oxygen during an ischemic event, a resultant increase in intracellular calcium levels, followed by reoxygenation and the concomitant generation of reactive oxygen species during reperfusion (Piper, H. M., Abdallah, C., Schafer, C., The first minutes of reperfusion: a window of opportunity for cardioprotection. Annals of Thoracic Surgery 2003, 75:644; Yellon, D. M., Hausenloy, D. J., Myocardial reperfusion injury. New England Journal of Medicine 2007, 357:1121). Reperfusion injury may be responsible for as much as 50% of the damage to the heart following a myocardial infarction (Yellon, D. M., Hausenloy, D. J., Myocardial reperfusion injury. New England Journal of Medicine 2007, 357:1121).

The prevalence of cardiovascular disease in the United States, and throughout the world, necessitates the development of therapies and therapeutic agents that can effectively prevent, reduce, or counteract ischemia and ischemia-reperfusion injury resulting from a heart attack or stroke. Current therapies for treating ischemia and ischemia-reperfusion injury caused by myocardial infarction, such as mechanical ischemic preconditioning, have proven to be clinically impractical, while other therapies, such as antagonists to block the influx of calcium and scavengers of reactive oxygen species, have yielded disappointing clinical outcomes (Otani, H., Ischemic preconditioning: From molecule mechanisms to therapeutic opportunities. Antioxidants & Redox Signaling, 2008, 10:207; Yellon, D. M., Hausenloy, D. J., Myocardial reperfusion injury. New England Journal of Medicine 2007, 357:1121).

Thus, there is a significant need for new and more effective therapies and therapeutic agents for the treatment of ischemia and ischemia-reperfusion injuries resulting from cardiovascular disease and other conditions.

SUMMARY OF THE INVENTION

The invention described herein addresses a need for treating ischemia and ischemia-reperfusion injury, including myocardial ischemia and ischemia-reperfusion injury, by activating kinases involved in cell signaling pathways that inhibit apoptosis and by scavenging reactive oxygen species. In particular, the present invention relates to compositions comprising the disclosed compounds, or pharmaceutically acceptable salts thereof, and their effective use as activators of cytoprotective kinases.

In one embodiment, the invention relates to compositions comprising a substantially pure compound represented by Structural Formula I:

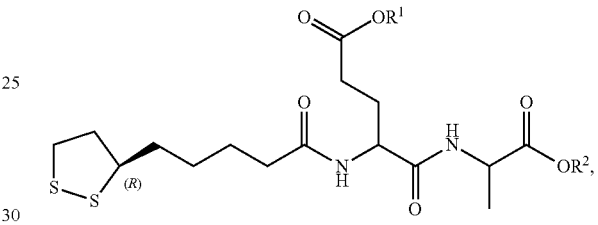

wherein R1 and R2 are each independently H or a hydrolyzable group, or a pharmaceutically acceptable salt thereof.

In another embodiment, the invention relates to compositions comprising a substantially pure compound represented by Structural Formula II:

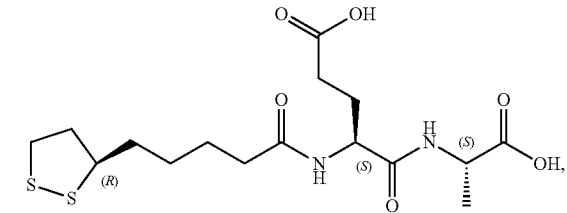

or a pharmaceutically acceptable salt thereof.

In a further embodiment, the invention relates to compositions comprising a substantially pure compound represented by Structural Formula III:

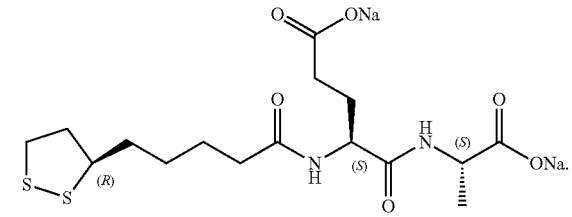

In another embodiment, the invention relates to a composition comprising: i) a pharmaceutically acceptable carrier or diluent; and ii) a substantially pure compound represented by Structural Formula I:

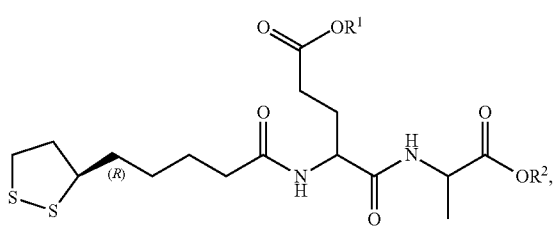

wherein R1 and R2 are each independently H or a hydrolyzable group, or a pharmaceutically acceptable salt thereof.

In an additional embodiment, the invention relates to a method of activating at least one cytoprotective kinase (e.g., Akt kinase, IRK kinase, IGF1R kinase, Src kinase) in a cell, comprising contacting the cell with an effective amount of a compound represented by Structural Formula I:

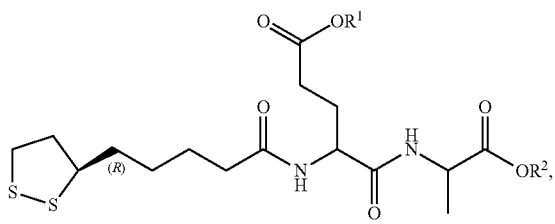

wherein R1 and R2 are each independently H or a hydrolyzable group, or a pharmaceutically acceptable salt thereof. In a particular embodiment, the cytoprotective kinase is Akt kinase, or a kinase that functions in the same cell signaling pathway as Akt kinase (e.g., IRK kinase).

In another embodiment, the invention relates to a method of treating an ischemia or ischemia-reperfusion injury in a mammalian subject, comprising administering to the subject an effective amount of a compound represented by Structural Formula I:

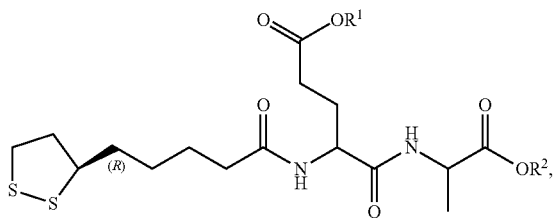

wherein R1 and R2 are each independently H or a hydrolyzable group, or a pharmaceutically acceptable salt thereof. In a particular embodiment, the ischemia or ischemia-reperfusion injury is a myocardial ischemia or ischemia-reperfusion injury.

In yet another embodiment, the invention relates to a method of inhibiting apoptosis in a subject, comprising administering to the subject an effective amount of a compound represented by Structural Formula I:

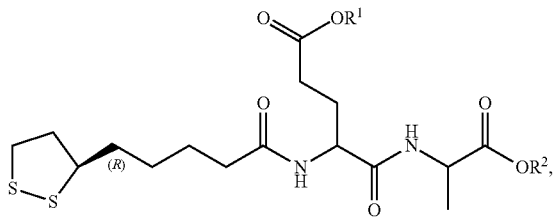

wherein R1 and R2 are each independently H or a hydrolyzable group, or a pharmaceutically acceptable salt thereof.

In a further embodiment, the invention relates to a method of preventing cytosolic calcium overload in a subject, comprising administering to the subject an effective amount of a compound represented by Structural Formula I:

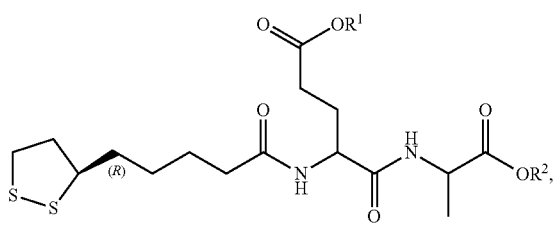

wherein R1 and R2 are each independently H or a hydrolyzable group, or a pharmaceutically acceptable salt thereof.

In another embodiment, the invention relates to a method of increasing peroxyl radical absorbance in a subject (e.g., a subject suffering from ischemia), comprising administering to the subject an effective amount of a compound represented by Structural Formula I:

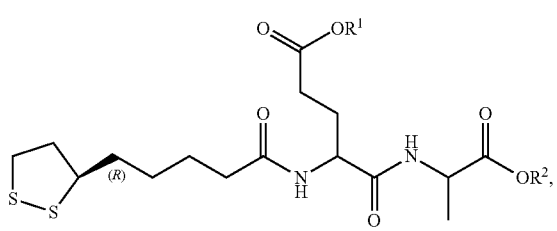

wherein R1 and R2 are each independently H or a hydrolyzable group, or a pharmaceutically acceptable salt thereof.

DETAILED DESCRIPTION OF THE INVENTION

Definitions

Figure 1:
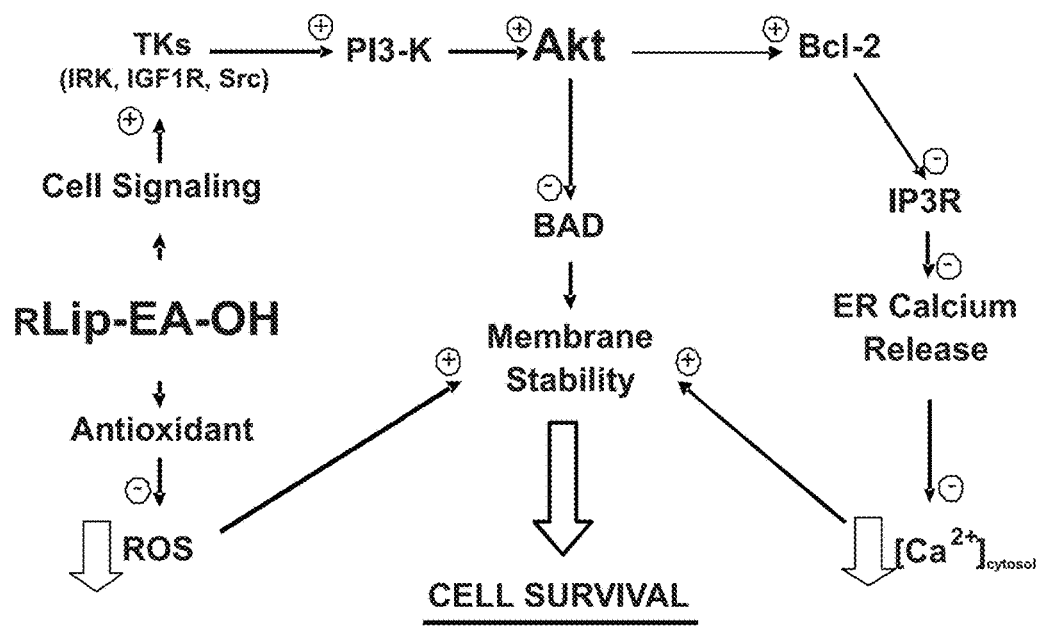
FIG. 1 is a diagram depicting proposed cell signaling pathways accounting for the potential mechanisms of action for rLip-EA-OH and related compounds.

The term "alkyl" means a straight or branched hydrocarbon radical having 1-10 carbon atoms and includes, for example, methyl, ethyl, n-propyl, isopropyl, n-butyl, sec.-butyl, isobutyl, tert.-butyl, n-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl, cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like.

The term "aryl" means an aromatic radical which is a phenyl group, a naphthyl group, an indanyl group or a tetrahydronaphthalene group. An aryl group is optionally substituted with 1-4 substituents. Exemplary substituents include alkyl, alkoxy, alkylthio, alkylsulfonyl, halogen, trifluoromethyl, dialkylamino, nitro, cyano, CO2H, CONH2, N-monoalkyl-substituted amido and N,N-dialkyl-substituted amido.

The term "heteroaryl" means a 5- or 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A heteroaryl is optionally substituted. Exemplary substituents include alkyl, alkoxy, alkylthio, alkylsulfonyl, halogen, trifluoromethyl, dialkylamino, nitro, cyano, CO2H, CONH2, N-monoalkyl-substituted amido and N,N-dialkyl-substituted amido, or by oxo to form an N-oxide.

The term "heterocyclyl" means a 4-, 5-, 6- or 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide. A heterocyclyl can be optionally substituted with 1-4 substituents. Exemplary substituents include alkyl, haloalkyl and oxo.

Certain of the disclosed compounds may exist in various stereoisomeric forms. Stereoisomers are compounds that differ only in their spatial arrangement. Enantiomers are pairs of stereoisomers that are non-superimposable mirror images of one another, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol " " in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Levorotatory" signifies that polarized light is rotated to the left when passed through an asymmetric compound. The prefix to designate levorotary is "l".

"Dextrorotatory" signifies that polarized light is rotated to the right when passed through an asymmetric compound. The prefix to designate levorotary is "d".

"Geometric isomer" means isomers that differ in the orientation of substituent atoms in relationship to a carbon-carbon double bond, to a cycloalkyl ring, or to a bridged bicyclic system. Atoms (other than hydrogen) on each side of a carbon-carbon double bond may be in an E (substituents are on opposite sides of the carbon-carbon double bond) or Z (substituents are oriented on the same side) configuration.

When the stereochemistry of a disclosed compound is named or depicted by structure, the named or depicted stereoisomer is at least 60%, 70%, 80%, 90%, 99% or 99.9% by weight relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound has at least one chiral center and is named or depicted by structure without indicating the stereochemistry, it is to be understood that the name or structure encompasses one enantiomer of the compound free from the corresponding optical isomer, a racemic mixture of the compound and mixtures enriched in one enantiomer relative to its corresponding optical isomer.

When a disclosed compound has at least two chiral centers and is named or depicted by structure without indicating the stereochemistry, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

In compounds of the invention that contain one or more double bonds, the designations "E," "Z," "cis," and "trans" indicate configurations relative to the core molecule.

Amino acids may exist in various stereoisomeric forms. The Fischer convention is commonly used to describe the configuration of the groups around the asymmetric carbon atom of an amino acid as compared to the arrangement of the groups around the asymmetric carbon atom of glyceraldehyde. For α-amino acids, the amino, carboxyl, R (i.e., the side chain) and H groups around the Cα atom correspond to the hydroxyl, aldehyde, CH2OH, and H groups, respectively, of glyceraldehyde:

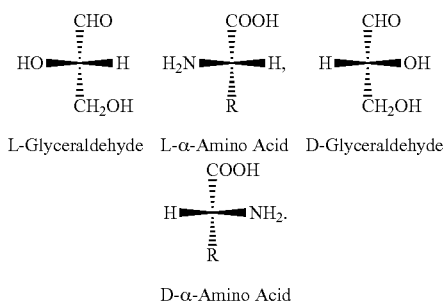

L-Glyceraldehyde   L-α-Amino Acid   D-Glyceraldehyde

D-α-Amino Acid

L-Glyceraldehyde and L-α-amino acids have the same relative configuration and D-glyceraldehyde and D-α-amino acids have the same relative configuration. The L or D designation does not indicate the amino acid's ability to rotate the plane of polarized light. Many L-amino acids are dextrorotatory.

As used herein, "substantially pure" means that the depicted or named compound is at least about 60% by weight. For example, "substantially pure" can mean about 60%, 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a percentage between 70% and 100%. In one embodiment, substantially pure means that the depicted or named compound is at least about 75%. In a specific embodiment, substantially pure means that the depicted or named compound is at least about 90% by weight. The substantially pure composition comprising a compound represented by Structural Formula I can comprise the four compounds represented by Structural Formulae IV, V, VI or VII, either alone, or in any combination thereof.

As used herein, an "effective amount" is an amount sufficient to achieve a desired effect under the conditions of administration, in vitro, in vivo or ex vivo, such as, for example, an amount sufficient to activate one or more cytoprotective kinases in a cell, an amount sufficient to inhibit apoptosis of a cell and an amount sufficient to inhibit (e.g., prevent, delay) ischemia and ischemia reperfusion injury (e.g., in a subject). The effectiveness of a therapy can be determined by suitable methods known by those of skill in the art including those described herein.

As defined herein, a "therapeutically effective amount" is an amount sufficient to achieve a desired therapeutic or prophylactic effect in a subject in need thereof under the conditions of administration, such as, for example, an amount sufficient to inhibit (e.g., prevent, delay) ischemia and ischemia reperfusion injury in a subject (e.g., by inhibiting apoptosis of one or more affected cells in the subject). The effectiveness of a therapy can be determined by suitable methods known by those of skill in the art.

The present invention is based, in part, on Applicants' discovery that the lipoic acid derivative compounds described herein have cytoprotective and anti-oxidative properties. In particular, Applicants have shown that a certain lipoic acid derivative, RLip-EA-OH, activates Akt kinase and other kinases (e.g., IRK, IGF1R, Src) that are known to mediate cell signaling pathways that inhibit apoptosis and promote cell survival (FIG. 1). Applicants have further shown that RLip-EA-OH can reduce the extent of ischemia and ischemia-reperfusion injury in an animal model of myocardial ischemia-reperfusion injury.

In one embodiment, the invention relates to compositions comprising a substantially pure compound represented by Structural Formula I:

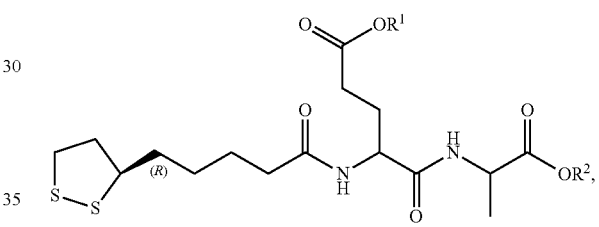

wherein R1 and R2 are each independently H or a hydrolyzable group, or a pharmaceutically acceptable salt thereof.

As used herein, the term "hydrolyzable group" refers to a moiety that, when present in a molecule of the invention, yields a carboxylic acid or salt thereof upon hydrolysis. Hydrolysis can occur, for example, spontaneously under acidic or basic conditions in a physiological environment (e.g., blood, metabolically active tissues such as, for example, liver, kidney, lung, brain), or can be catalyzed by an enzyme(s), (e.g., esterase, peptidases, hydrolases, oxidases, dehydrogenases, lyases or ligases). A hydrolyzable group can confer upon a compound of the invention advantageous properties in vivo, such as improved water solubility, improved circulating half-life in the blood, improved uptake, improved duration of action, or improved onset of action.

In one embodiment, the hydrolyzable group does not destroy the biological activity of the compound. In an alternative embodiment, a compound with a hydrolyzable group can be biologically inactive, but can be converted in vivo to a biologically active compound.

Compounds of the invention that include hydrolyzable groups may act as prodrugs. As used herein, the term "prodrug" means a compound that can be hydrolyzed, oxidized, metabolized or otherwise react under biological conditions to provide a compound of the invention. Prodrugs may become active upon such reaction under biological conditions, or they may have activity in their unreacted forms. A prodrug may undergo reduced metabolism under physiological conditions (e.g., due to the presence of a hydrolyzable group), thereby resulting in improved circulating half-life of the prodrug (e.g., in the blood). Prodrugs can typically be prepared using well-known methods, such as those described by Burger's Medicinal Chemistry and Drug Discovery (1995) 172-178, 949-982 (Manfred E. Wolff ed., 5th ed).

In one embodiment, the hydrolyzable group is selected from the group consisting of (C1-C10)alkyl, (C2-C10)alkenyl, (C2-C10)alkynyl, (C1-C10)alkoxy(C1-C10)alkyl, (C1-C10)alkoxy(C1-C10)alkoxy(C1-C10)alkyl, aryl and aryl(C1-C10)alkyl, wherein each is optionally substituted with 1 to 3 substituents selected from the group consisting of halo, nitro, cyano, cyclopropyl, cyclobutyl, cyclopentyl, cyclohexyl, amino, (C1-C6)alkylamino, di(C1-C6)alkylamino, (C1-C6)alkyl, halo(C1-C6)alkyl, (C1-C6)alkoxy, halo(C1-C6)alkoxy, morpholino, phenyl, and benzyl.

In another embodiment, the hydrolyzable group is selected from the group consisting of methyl, ethyl, n-propyl, isopropyl, n-butyl, sec-butyl, isobutyl, tert-butyl, pentyl, hexyl, heptyl, allyl, ethoxymethyl, methoxyethyl, methoxyethoxymethyl, methoxyethoxyethyl, benzyl, pentafluorophenyl, 2-N-(morpoholino)ethyl, dimethylaminoethyl and para-methoxybenzyl.

Hydrolysis of the hydrolyzable group generates a carboxylic acid. For example, the tert.-butyl in Compound A is cleaved to generate the carboxylic acid groups in Compound B in mildly acidic conditions:

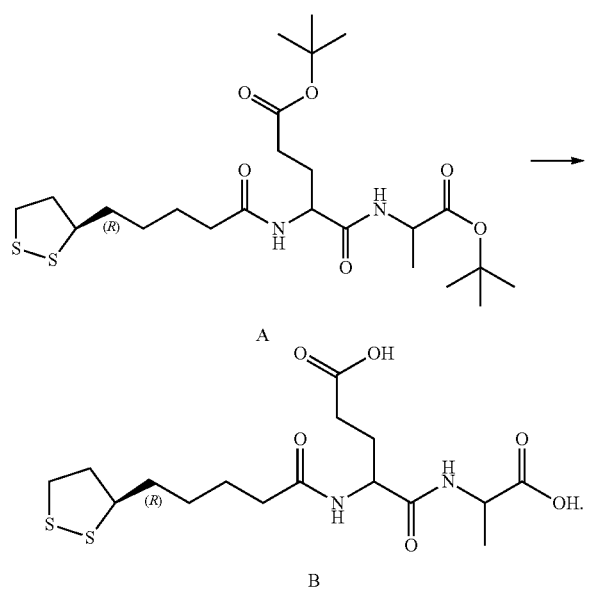

R1 and R2 may be different hydrolyzable groups, resulting in compounds such as Compound C, where two different esters are present. Use of different hydrolyzable groups can allow for selective hydrolysis of a particular ester. For example, either R1 or R2 can be a hydrolyzable group stable to acidic environments and the other can be a hydrolyzable group stable to basic environments. In an alternative embodiment, either R1 or R2 can be a hydrolyzable group cleaved by a particular enzyme, while the other is not cleaved by that enzyme. In some embodiments, the hydrolysis of the two esters may occur simultaneously. Alternatively, the hydrolysis of the two esters may be step-wise. In another example, the tert.-butyl group in Compound C is cleaved under mildly acidic conditions while the 2-N-morpolinoethyl moiety may be enzymatically cleaved with the lipase from R. niveus:

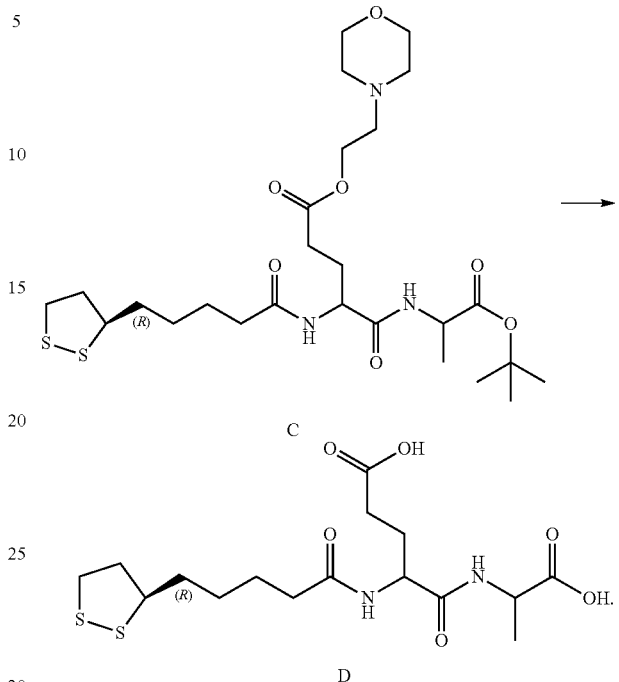

Methods for the selection, introduction and subsequent removal of hydrolyzable groups are well known to those skilled in the art. (T. W. Greene and P. G. M. Wuts "Protective Groups in Organic Synthesis" John Wiley & Sons, Inc., New York 1999).

Alternatively, only one of R1 or R2 may be present, resulting in a hydrolysis of a single ester to generate the carboxylic acid or salt thereof:

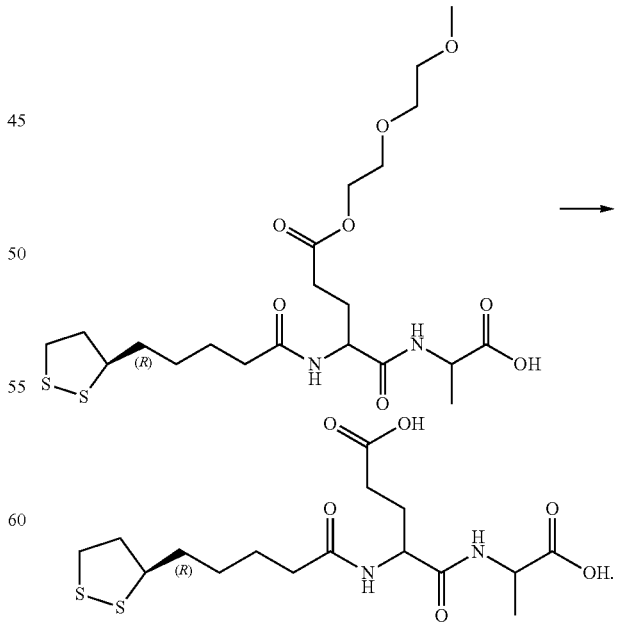

One skilled in the art will understand that other hydrolyzable protecting groups can be employed with the compounds of the present invention to obtain prodrugs encompassed by the present description.

The compounds of the invention may be present in the form of pharmaceutically acceptable salts. For use in medicines, the salts of the compounds of the invention refer to non-toxic pharmaceutically acceptable salts.

The pharmaceutically acceptable salts of the disclosed compounds include acid addition salts and base addition salts. The term "pharmaceutically acceptable salts" embraces salts commonly used to form alkali metal salts and to form addition salts of free acids or free bases. The nature of the salt is not critical, provided that it is pharmaceutically acceptable.

Suitable pharmaceutically acceptable acid addition salts of the disclosed compounds may be prepared from an inorganic acid or an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Pharmaceutically acceptable acidic/anionic salts also include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

Suitable pharmaceutically acceptable base addition salts of the disclosed compounds include, but are not limited to, metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine, arginine and procaine. All of these salts may be prepared by conventional means from the corresponding compound represented by the disclosed compound by treating, for example, the disclosed compounds with the appropriate acid or base. Pharmaceutically acceptable basic/cationic salts also include, the diethanolamine, ammonium, ethanolamine, piperazine and triethanolamine salts.

In an embodiment, the pharmaceutically acceptable salt comprises a monovalent cation or a divalent cation. In a particular embodiment, the pharmaceutically acceptable salt is a lysine salt.

In another embodiment, the monovalent cation is a monovalent metal cation and the divalent cation is a divalent metal cation. In a particular embodiment, the monovalent metal cation is a sodium cation.

In another embodiment, the invention relates to compositions comprising a substantially pure compound represented by Structural Formula II:

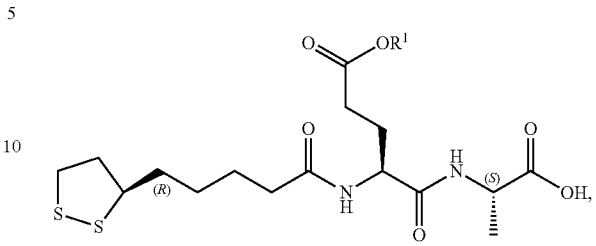

or a pharmaceutically acceptable salt thereof. As used herein, RLip-EA-OH refers to Structural Formula II.

In a further embodiment, the invention relates to compositions comprising a substantially pure compound represented by Structural Formula III:

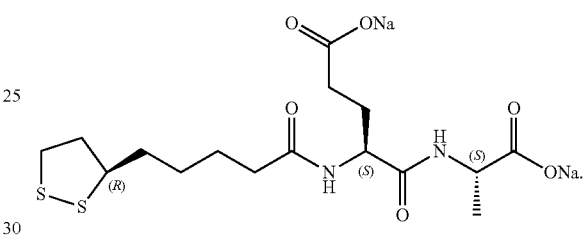

In another embodiment, the invention relates to compositions comprising a substantially pure compound represented by Structural Formula IV:

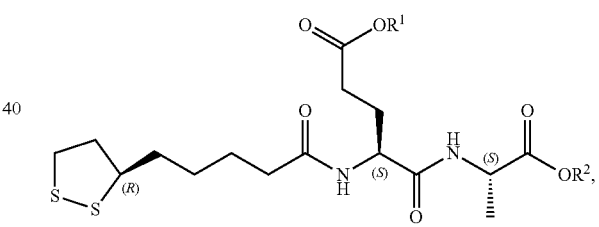

or a pharmaceutically acceptable salt thereof. The values of R1 and R2 are as defined above for Structural Formula (I).

In another embodiment, the invention relates to compositions comprising a substantially pure compound represented by Structural Formula V:

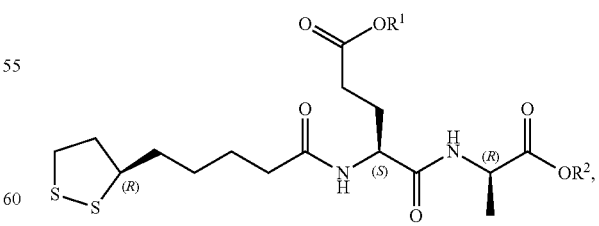

or a pharmaceutically acceptable salt thereof. The values of R1 and R2 are as defined above for Structural Formula (I).

In another embodiment, the invention relates to compositions comprising a substantially pure compound represented by Structural Formula VI:

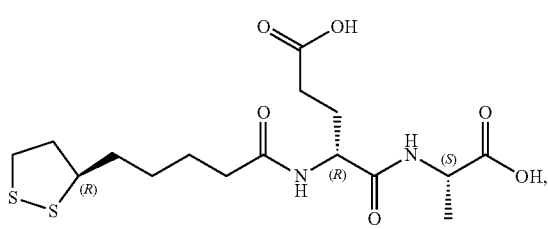

or a pharmaceutically acceptable salt thereof. The values of R1 and R2 are as defined above for Structural Formula (I).

In another embodiment, the invention relates to compositions comprising a substantially pure compound represented by Structural Formula VII:

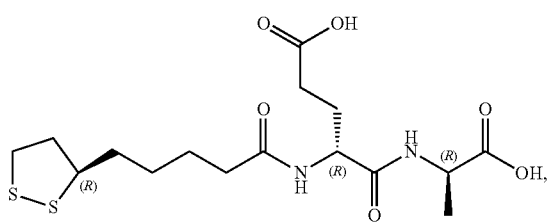

or a pharmaceutically acceptable salt thereof. The values of R1 and R2 are as defined above for Structural Formula (I).

A composition of the invention may, alternatively or in addition to the disclosed compounds, comprise a pharmaceutically acceptable salt of a compound represented by the disclosed compounds, or a prodrug or pharmaceutically active metabolite of such a compound or salt and one or more pharmaceutically acceptable carriers and are delivered to a recipient subject (preferably a human) in accordance with known methods of drug delivery. The compounds of the present invention may be administered alone or in combination with at least one other agent known or believed by the applicants to be useful for the activation of cytoprotective kinases and/or the treatment of ischemia or ischemia-reperfusion injuries.

Alternatively, a composition of the invention may comprise a compound represented by the disclosed compounds or a pharmaceutical salt thereof as the only pharmaceutically active agent in the composition.

In another embodiment, the invention relates to a composition comprising: i) a pharmaceutically acceptable carrier or diluent; and ii) a compound represented by Structural Formula I:

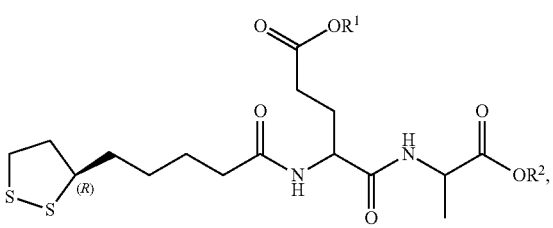

wherein R1 and R2 are each independently H or a hydrolyzable group, or a pharmaceutically acceptable salt thereof.

The pharmaceutically acceptable compositions of the present invention comprise one or more compounds disclosed herein in association with one or more nontoxic, pharmaceutically acceptable carriers and/or diluents and/or adjuvants and/or excipients, collectively referred to herein as "carrier" materials, and, if desired, other active ingredients.

The present invention also relates to methods of activating a cytoprotective kinase in a cell. As used herein, the term "cytoprotective kinase" refers to a kinase that, when activated, phosphorylates components of one or more cell signaling pathways that promote cell survival and/or inhibit cell death (e.g., apoptosis).

Accordingly, in one embodiment, the invention relates to a method of activating a cytoprotective kinase (e.g., insulin receptor kinase, Akt kinase, insulin-like growth factor 1 receptor kinase, Src kinase) in a cell, comprising contacting the cell with an effective amount of a compound represented by Structural Formula I:

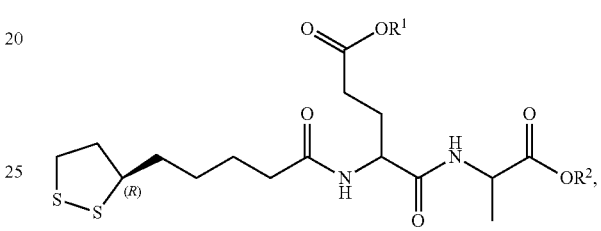

wherein R1 and R2 are each independently H or a hydrolyzable group, or a pharmaceutically acceptable salt thereof.

In a particular embodiment, the invention relates to a method of activating a kinase whose pathway is cytoprotective in a cell, comprising contacting the cell with an effective amount of a compound represented by Structural Formula II:

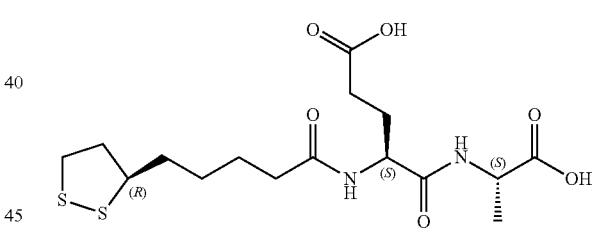

or a pharmaceutically acceptable salt thereof.

In another embodiment, the invention relates to a method of activating a cytoprotective kinase in a cell, comprising contacting the cell with an effective amount of a compound represented by Structural Formula III:

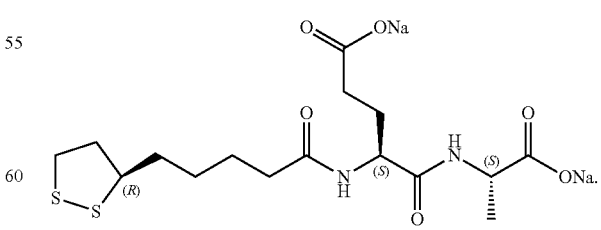

Activation of a cytoprotective kinase can lead to activation of one or more cytoprotective cell signaling pathways that include the cytoprotective kinase. In a particular embodiment, activation of one or more cytoprotective kinases in a cell by the compounds of the invention can inhibit (e.g., prevent, delay) apoptosis of the cell in which the kinase(s) has been activated.

The methods of the invention relating to activation of cytoprotective kinases can be performed in vitro (e.g., using cultured cells, using isolated cells) or in vivo (e.g., by administering a compound(s) of the invention to a living organism). In a particular embodiment, the compounds of the invention are used in a method to activate one or more cytoprotective kinases in one or more cells in a human.

In one embodiment, the cytoprotective kinase is Akt kinase. Activation of Akt kinase can lead to activation of one or more Akt cell signaling pathways that are cytoprotective. Akt kinase, also known as Akt, PKB and Rac-PK, belongs to the Akt/PKB family of serine/threonine kinases and has been shown to be involved in many diverse signaling pathways (Alessi, and Cohen, Curr. Opin. Genet. Dev. 8 (1998), 55-62) including pathways related to cell survival and proliferation (Song, G., Ouyang, G., and Bao, S., The activation of Akt/PKB signaling pathway and cell survival. J Cell Mol Med 2005 9:59; Hausenloy, D. J., Yellon, D. M., Reperfusion injury salvage kinase signaling: taking a RISK for cardioprotection. Heart Fail Rev 2007, 12:217.). Akt consists of an N-terminal lipid-binding pleckstrin-homology domain and a C-terminal catalytic domain. In resting cells, all Akt isoforms reside in the cytoplasm but translocate to the plasma membrane following stimulation with external ligands. Translocation and subsequent activation is induced by several different ligands including PDGF, IGF, EGF, βFGF and insulin. This activation depends on PI3-kinase activity and requires hierarchial phosphorylation of Thr308 and Ser473 of Akt by PDK-1 and PDK-2, respectively (Alessi et al., Curr. Biol. 8 (1998), 69-81). Once activated, Akt mediates several different functions, including prevention of apoptosis, induction of differentiation and/or proliferation, protein synthesis and the metabolic effects of insulin.

As described in Example 2 herein, compounds of the invention increase Akt phosphorylation in a cell-based in vitro assay. Akt kinase phosphorylation in a cell can be assessed using one or more in vitro Akt kinase phosphorylation assays known in the art including, for example, kits and assays for testing AKT phosphorylation in cells available from commercial suppliers (e.g., Cellomics Phospho-AKT Activation Kit, Thermo Scientific; Akt Activity Assay Kit, BioVision Incorporated; FACE™ AKT in-cell Western analysis for phospho AKT (S473), Active Motif; PathScan® Phospho-Akt (Thr308) Sandwich ELISA Kit, Cell Signaling Technology; AlphaScreen® SureFire® Phospho-AKT Assay Kits, Perkin Elmer; Akt Activity Immunoassay Kit, EMD Biosciences). An exemplary assay for assessing Akt kinase phosphorylation is described herein in Example 2. (Chen, H., Kovar, J., Sissons, S., et. al. A cell based immunocytochemical assay for monitoring kinase signaling pathways and drug efficacy. Analyt Biochem 2005 338: 136)

Akt activation can also be assessed in vivo, e.g., by immunodetection methods performed on a cell sample obtained from a subject. Several Akt-specific antibodies, including phospho-specific Akt antibodies (e.g., specific for phospho-Ser473, specific for phospho-Thr308), are commercially available (e.g., Perkin Elmer).

In another embodiment, the cytoprotective kinase is insulin receptor kinase ("IRK") (Diesel, B., Kulhanek-Heinze, S., Holtje, M., et. al., αα-Lipoic Acid as a directly binding activator of the insulin receptor: protection from hepatocyte apoptosis. Biochemistry, 2007 46:2146; Hausenloy, D. J., Yellon, D. M. New directions for protecting the heart against ischemia-reperfusion injury: targeting the reperfusion injury salvage kinase (RISK)-pathway. Cardiovasc Res 2004 61:448). IRK activation leads to phosphorylation and activation of Akt (Alessi, D. R., Andjelkovic, M., Caudwell, B., Cron, P., Morrice, N., Cohen, P., Hemmings, B. A. Mechanism of activation of protein kinase B by insulin and IGF-1. EMBO J 1996 15:6541-6551). Activation of IRK can lead to activation of one or more IRK cell signaling pathways that are cytoprotective. As described in Example 3 herein, compounds of the invention activate IRK in a biochemical assay in vitro. IRK activation can be assessed using one or more in vitro IRK activation assays known in the art. An exemplary assay for assessing IRK activation is described herein in Example 3. (Mobility Shift Kinase Assay, Caliper Life Sciences, Hanover, Md.)

In another embodiment, the cytoprotective kinase is insulin-like growth factor 1 receptor ("IGF1R") kinase. Activation of IGF1R kinase can lead to activation of one or more IGF1R cell signaling pathways that are cytoprotective. As described in Example 4 herein, compounds of the invention activate IGF1R kinase in a biochemical assay in vitro. IGF1R kinase activation can be assessed using one or more in vitro IGF1R kinase activation assays known in the art. An exemplary assay for assessing IGF1R kinase activation is described herein in Example 4.

In a further embodiment, the cytoprotective kinase is Src kinase. Activation of Src kinase can lead to activation of one or more Src cell signaling pathways that are cytoprotective. As described in Example 4 herein, compounds of the invention activate Src kinase in a biochemical assay in vitro. Src kinase activation can be assessed using one or more in vitro Src kinase activation assays known in the art.

IGF1R and Src tyrosine kinases play a role in protecting the heart from ischemia-reperfusion injury (Buddhadeb, D., Takano, H., Tang, X.-L., et al. Role of Src protein tyrosine kinase in late preconditioning against myocardial infarction. Am J Physiol 2002 283:H549; Pasdois, P., Quinlan, C. L., Rissa, A., et al. Ouabain protects rat hearts against ischemia-reperfusion injury via pathway involving Src kinase, mitoKATP, and ROS. Am J Physiol 2006, 292:H1470; Suzuki, Y. J. Growth factor signaling for cardioprotection against oxidative stress-induced apoptosis. Antiox Redox Signal 2003, 5:741; Hausenloy, D. J., Yellon, D. M., New directions for protecting the heart against ischaemia-reperfusion injury: Targeting the Reperfusion Injury Salvage Kinase (RISK)-pathway. Cardiovasc Res 2004 61:448).

According to the invention, activation of one or more cytoprotective kinases in a cell by the compounds of the invention can inhibit (e.g., prevent, delay) apoptosis of the cell. Methods of assessing apoptosis are well known in the art. Microscopic analysis (e.g., light microscopy, electron microscopy, confocal microscopy, laser-scanning microscopy) for visualizing apoptotic cells (e.g., by detecting morphological changes associated with apoptosis, such as chromatin condensation and cytoplasmic shrinking) is typically employed to study apoptotic cells.

The study of DNA fragmentation in agarose gels is also considered to be indicative of apoptosis. A number of techniques take advantage of DNA fragmentation for labeling the fragments and thus for quantifying the proportion of apoptotic cells. Each DNA fragment has a 3'-OH terminal portion. This terminal fragment can be labeled in various ways (for instance, with the help of a modified terminal deoxynucleotidyl transferase), so that the labeling rate is proportional to the degree of DNA fragmentation.

In particular, TdT-mediated dUTP Nick-End Labeling, or TUNEL, is a technique for detecting fragmented DNA, which occurs near the final step in the apoptotic process. Fragmented DNA of apoptotic cells can incorporate fluorescein-dUTP at 3'-OH at DNA ends using the enzyme Terminal Deoxynucleotidyl Transferase (TdT), which forms a polymeric tail using the principle of the TUNEL assay. The labeled DNA can then be visualized directly by fluorescence microscopy or quantitated by flow cytometry.

Some current techniques take advantage of the changes in membrane phospholipids that occur early in apoptotic cells. The negatively charged membrane phospholipids exposed to the external environment by the apoptotic cell are labeled with fluorochrome-conjugated molecules, and the percentage of fluorescent cells can be easily quantified.

Apoptosis can also be detected using fluorescently-conjugated Annexin V. Annexin V is an anticoagulant protein that preferentially binds negatively charged phospholipids. An early step in the apoptotic process is disruption of membrane phospholipid asymmetry, exposing phosphatidylserine (PS) on the outer leaflet of the cytoplasmic membrane. Fluorescently conjugated Annexin V can be used to detect this externalization of phosphatidylserine on intact living cells. Propidium iodide is often combined as a second flurochrome to detect necrotic cells. Induction of apoptosis leads to procaspase-3 proteolytic cleavage to generate an active 18 kDa caspase-3 fragment which then targets key modulators of the apoptotic pathway including poly-ADP-ribose polymerase and other caspases, for cleavage. Assays for detecting other active caspases in apoptotic cells are known in the art (e.g., Caspase-Glo® Assays, Promega).

Apoptotic cells can also be detected using the active 18 kDa caspase-3 fragment as a marker. Induction of apoptosis leads to procaspase-3 proteolytic cleavage to generate an active 18 kDa caspase-3 fragment which then targets key modulators of the apoptotic pathway, including poly-ADP-ribose polymerase and other caspases, for cleavage. Several antibodies that recognize only the active 18 kDa fragment are available from commercial suppliers (e.g., BD Biosciences, Chemicon, Cell Signaling Technology, Trevigen).

In addition, flow cytometry assays can be employed to monitor and quantify nuclear changes associated with apoptotic cells.

An exemplary assay for detecting inhibition of apoptosis is described herein in Example 5.

The activation of cellular cytoprotective kinases also have utility in the treatment of conditions resulting from excess or unwanted apoptotic cell death in an affected tissue or organ, leading to damage and dysfunction. Such conditions include, inter alia, ischemia and ischemia-reperfusion injury. Accordingly, the invention also relates to methods of treating an ischemia or ischemia-reperfusion injury in a mammalian subject, comprising administering to the subject an effective amount of a compound represented by Structural Formula I:

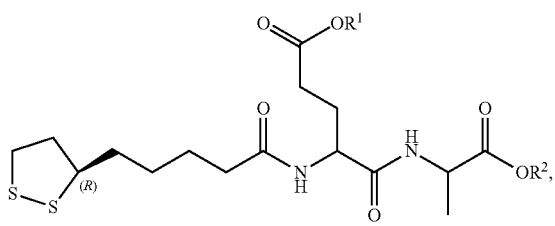

wherein R1 and R2 are each independently H or a hydrolyzable group, or a pharmaceutically acceptable salt thereof.

In a particular embodiment, the invention relates to a method of treating an ischemia or ischemia-reperfusion injury in a mammalian subject, comprising administering to the subject an effective amount of a compound represented by Structural Formula II:

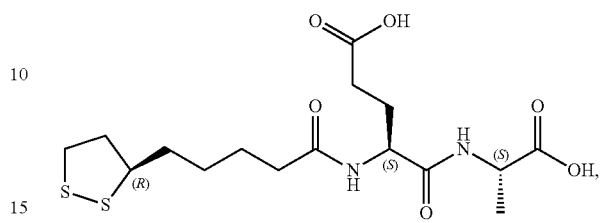

or a pharmaceutically acceptable salt thereof.

In another embodiment, the invention relates to a method of treating an ischemia or ischemia-reperfusion injury in a mammalian subject, comprising administering to the subject an effective amount of a compound represented by Structural Formula III:

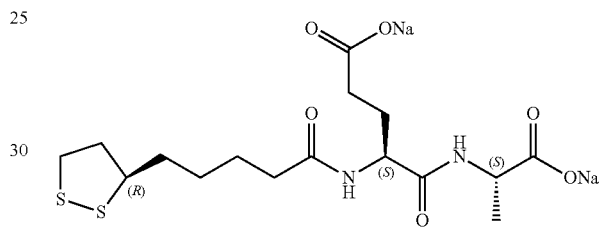

As used herein, the "injury resulting from ischemia," "injury caused by ischemia" and "ischemic injury" refer to an injury to a cell, tissue or organ caused by ischemia, or an insufficient supply of blood (e.g., due to a blocked artery), and, thus, oxygen, resulting in damage or dysfunction of the tissue or organ (Piper, H. M., Abdallah, C., Schafer, C., Annals of Thoracic Surgery 2003, 75:644; Yellon, D. M., Hausenloy, D. J., New England Journal of Medicine 2007, 357:1121). Injuries that result from ischemia can affect various tissues and organs. Such injuries may be treated by the compounds and methods of the invention, including, for example, injuries caused by cardiovascular ischemia, cerebrovascular ischemia, renal ischemia, hepatic ischemia, ischemic cardiomyopathy, cutaneous ischemia, bowel ischemia, intestinal ischemia, gastric ischemia, pulmonary ischemia, pancreatic ischemia, skeletal muscle ischemia, abdominal muscle ischemia, limb ischemia, ischemic colitis, mesenteric ischemia and silent ischemia. Thus, an injury resulting from ischemia can affect, for example, a heart, kidney, liver, brain, muscle, intestine, stomach, lung or skin.

In a particular embodiment, the injury resulting from ischemia is the result of a myocardial ischemia. An injury resulting from a myocardial ischemia can result from, for example, a myocardial infarction (e.g., an acute myocardial infarction) in an individual.

In another embodiment, the injury resulting from ischemia is an injury resulting from cerebral ischemia (e.g., a stroke) in an individual.

In another embodiment, the injury resulting from ischemia is an ischemia-reperfusion injury. As used herein, the term "ischemia-reperfusion injury" refers to an injury resulting from the restoration of blood flow to an area of a tissue or organ that had previously experienced deficient blood flow due to an ischemic event. Oxidative stresses associated with reperfusion may cause damage to the affected tissues or organs. Ischemia-reperfusion injury is characterized biochemically by a depletion of oxygen during an ischemic event followed by reoxygenation and the concomitant generation of reactive oxygen species during reperfusion (Piper, H. M., Abdallah, C., Schafer, C., Annals of Thoracic Surgery 2003, 75:644; Yellon, D. M., Hausenloy, D. J., New England Journal of Medicine 2007, 357:1121).

An ischemia-reperfusion injury can be caused, for example, by a natural event (e.g., restoration of blood flow following a myocardial infarction), a trauma, or by one or more surgical procedures or other therapeutic interventions that restore blood flow to a tissue or organ that has been subjected to a diminished supply of blood. Such surgical procedures include, for example, coronary artery bypass graft surgery, coronary angioplasty, organ transplant surgery and the like. In a particular embodiment the compounds and methods of the invention are useful for treating peri-operative cardiac damage caused by an ischemia or ischemia-reperfusion injury.

For the treatment of ischemic and ischemia-reperfusion injuries caused by therapeutic interventions, such as surgical procedures, it is preferable that a compound of the invention is administered to a subject undergoing treatment prior to the therapeutic intervention (e.g., cardiac surgery, organ transplant). For example, a compound of the invention can be administered to a subject undergoing treatment, e.g., about 1 hour, about 2 hours, about 3 hours, about 4 hours, about 5 hours, about 12 hours, about 24 hours, or about 48 hours prior to the therapeutic intervention. A compound of the invention can also be administered to a subject undergoing treatment, for example, about 5 minutes, about 10 minutes, about 15 minutes, about 20 minutes, about 30 minutes or about 45 minutes prior to the therapeutic intervention.

Alternatively, or in addition, a compound of the invention can be administered to a subject undergoing treatment at the time of, or during, the therapeutic intervention. For example, the compound can be administered one or more times during the course of a therapeutic intervention in intervals (e.g., 15 minute intervals). Alternatively, a compound can be administered continuously throughout the duration of a therapeutic intervention.

Furthermore, a compound of the invention can be administered to a subject undergoing treatment after a therapeutic intervention. For example, a compound of the invention can be administered to a subject undergoing treatment, e.g., about 1 hour, about 2 hours, about 3 hours, about 4 hours, about 5 hours, about 12 hours, about 24 hours, or about 48 hours after the therapeutic intervention. A compound of the invention can also be administered to a subject undergoing treatment, for example, about 5 minutes, about 10 minutes, about 15 minutes, about 20 minutes, about 30 minutes or about 45 minutes after the therapeutic intervention.

A compound of the invention can also be used to inhibit an ischemia or ischemia-reperfusion injury to a cell, tissue or organ, ex vivo, prior to a therapeutic intervention (e.g., a tissue employed in a graft procedure, an organ employed in an organ transplant surgery). For example, prior to transplant of an organ into a host individual (e.g., during storage or transport of the organ in a sterile environment), the organ can be contacted with a compound of the invention (e.g., bathed in a solution comprising a compound of the invention) to inhibit ischemia or ischemia-reperfusion injury.

As described herein, conditions resulting from ischemia, and injuries caused by ischemia or ischemia-reperfusion, can induce apoptotic cell death in an affected cell, tissue or organ, leading to damage and dysfunction. Accordingly, the compounds of the invention also have utility in methods of inhibiting apoptosis in a cell, a tissue or an organ (e.g., a transplant tissue or organ or a cell, tissue or organ in a subject), wherein the cell, tissue or organ has experienced an ischemia or other condition or disorder that results in excessive or unwanted apoptosis. The methods comprise contacting the cells, tissue, or organ with, or administering to the subject, an effective amount of a compound represented by Structural Formula I:

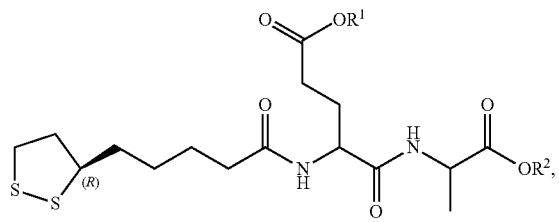

wherein R1 and R2 are each independently H or a hydrolyzable group, or a pharmaceutically acceptable salt thereof.

In a particular embodiment, the invention relates to a method of inhibiting apoptosis in a cell, tissue or organ, wherein the cell, tissue or organ has experienced an ischemia or other condition or disorder that results in excessive or unwanted apoptosis, comprising administering to the subject an effective amount of a compound represented by Structural Formula II:

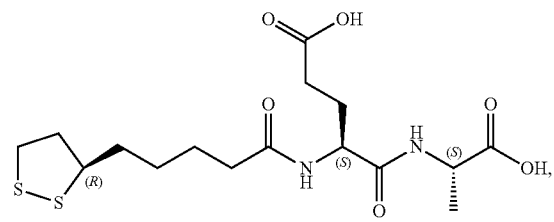

or a pharmaceutically acceptable salt thereof.

In another embodiment, the invention relates to a method of inhibiting apoptosis in a cell, tissue or organ, wherein the cell, tissue or organ has experienced an ischemia or other condition or disorder that results in excessive or unwanted apoptosis, comprising administering to the subject an effective amount of a compound represented Structural Formula III:

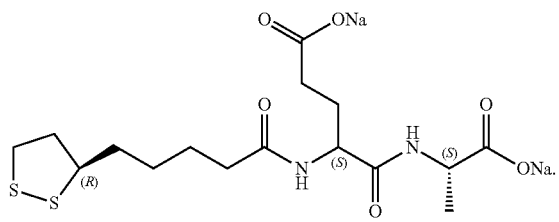

Methods for assessing apoptosis in cells, tissues or organs are known in the art and include those described herein.

Conditions associated with unwanted and/or excess apoptosis that are treatable by the compounds and methods of the invention include, but are not limited to, neurodegenerative diseases associated with excess apoptosis (e.g., Parkinson's Disease, Alzheimer's Disease, amyotrophic lateral sclerosis, retinitis pigmentosa, epilepsy), haematologic diseases associated with excess apoptosis (e.g., aplastic anaemia, myelodysplastic syndrome, T CD4+ lymphocytopenia, G6PD deficiency), tissue damage associated with excess apopotosis (e.g., myocardial infarction, cerebrovascular accident, ischemic renal damage, polycystic kidney disease), AIDS, and preeclampsia.

One of the hallmarks of ischemia-reperfusion injury is an increase in cytosolic calcium levels, resulting from a depletion of oxygen during an ischemic event (Piper, H. M., Abdallah, C., Schafer, C., Annals of Thoracic Surgery 2003, 75:644; Yellon, D. M., Hausenloy, D. J., New England Journal of Medicine 2007, 357:1121). It has been postulated that the increase in cytosolic calcium combined with an increase in free radicals triggers apoptosis (Chen, X., Zhang, X., Hubo, H., et al., Circ Res 2005, 97:1009; Lopes-Neblina, F., Toledo, A. H., Toledu-Pereyra, L. H. J Invest Surg 2005, 18:335). However, to date, treatments of patients with acute myocardial infarction with either an antagonist to block the influx of calcium or with a scavenger of the reactive oxygen species has each yielded disappointing clinical outcomes (Yellon, D. M., Hausenloy, D. J., New England Journal of Medicine 2007, 357:1121).

In addition, through pro-survival pathways activated by Akt, cytosolic calcium overload is inhibited (Joseph, S. K., Hajnoczky, G., Apoptosis 2007, 12:951; Pinton, P., Rizzuto, R., Cell Death Diff 2006, 13:1409; Khan, M. T., Wagner, L. II, Yule, D. I., Bhanumathy, C., Joseph, S. K. 2006, Akt kinase phosphorylation of inositol 1,4,5-triphosphate receptors. J Biol Chem 281:3731). The Akt dependent signaling pathway also prevents intracellular calcium overload by regulation of Bcl-2 (Raphael, J., Abedat, S., Rivo, J., et al., J Pharmacol Exp Ther 2006, 318:186; Thomenius, M. J. and Distelhorst, C. W., J Cell Sci 2003, 116:4493).

Accordingly, the compounds of the invention, which induce Akt activation, also have utility in methods of decreasing cytosolic calcium in a cell, tissue or organ (e.g., in a subject suffering from an ischemia). The methods comprise administering to the subject an effective amount of a compound represented by Structural Formula I:

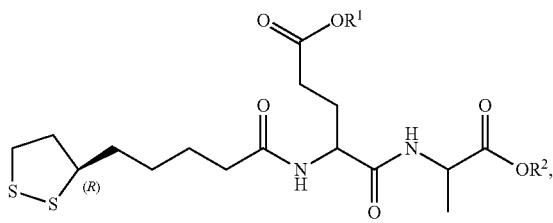

wherein R1 and R2 are each independently H or a hydrolyzable group, or a pharmaceutically acceptable salt thereof.

In a particular embodiment, the invention relates to a method of decreasing cytosolic calcium in a cell, tissue or organ, comprising administering to the subject an effective amount of a compound represented by Structural Formula II:

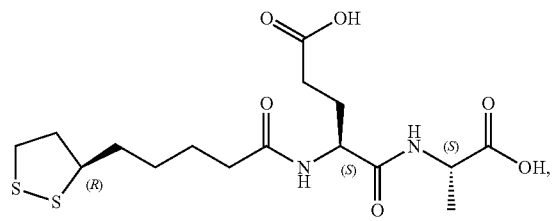

or a pharmaceutically acceptable salt thereof.

In another embodiment, the invention relates to a method of decreasing cytosolic calcium in a cell, tissue or organ, comprising administering to the subject an effective amount of a compound represented Structural Formula III:

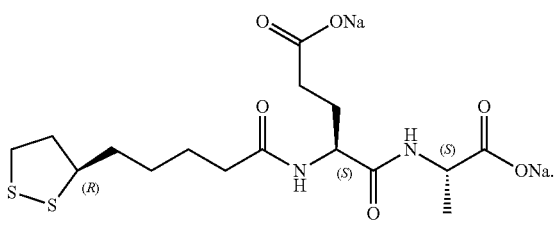

An exemplary assay for detecting levels of cytosolic calcium is described herein in Example 6.

Compounds of the invention also display an enhanced capacity for peroxyl radical absorbance. Biological organisms generate harmful reactive oxygen species (ROS) and various free radicals in the course of normal metabolic activities of tissues such as brain, heart, lung, and muscle tissue (Halliwell, B. and Gutteridge, J. M. C., eds. (Oxford: Clarendon Press, 1989)). Recognition of the role of ROS and free radicals in a variety of important diseases and drug side effects has grown appreciably over recent years. Many studies have demonstrated that a large number of disease states and harmful side effects of therapeutic drugs are linked with a failure of the antioxidant defense system of an individual to keep up with the rate of generation of ROS and various free radicals (see, for example, Chan, et al., Adv. Neurol., 1996, 71:271-279; DiGuiseppi, J. and Fridovich, I., Crit. Rev. Toxicol., 1984, 12:315-342). For example, abnormally high ROS levels have been found under conditions of anoxia elicited by ischemia during a stroke or anoxia generated in heart muscle during myocardial infarction (see, for example, Walton, M. et al., Brain Res. Rev., 1999, 29:137-168; Pulsinelli, W. A. et al., Ann. Neurol., 1982, 11: 499-502; Lucchesi, B. R., Am. J. Cardiol., 1990, 65:141-231). In addition, an elevation of ROS and free radicals has also been linked with reperfusion damage after renal transplants.

Accordingly, an elevation of ROS and free radicals has been linked with the progression and complications developed in many diseases, drug treatments, traumas, and degenerative conditions including oxidative stress induced damage with age, Tardive dyskinesia, Parkinson's disease, Huntington's disease, degenerative eye diseases, septic shock, head and spinal cord injuries, Alzheimer's disease, ulcerative colitis, human leukemia and other cancers, and diabetes (see, for example, Ratanis, Pharmaceutical Executive, pp. 74-80 (April 1991)).

For example, elevated levels of ROS and free radicals are known to be generated in cells and tissues during reperfusion after an ischemic event. Such increased levels of ROS and free radicals can cause considerable damage to an already stressed or debilitated organ or tissue. The compounds of this invention, which display peroxyl radical absorbance capacity, may be used to treat high levels of harmful free radicals present after reperfusion injuries that occur in diseases and conditions such as stroke, heart attack, or renal disease and kidney transplants. If the ischemic event has already occurred, as in stroke and heart attack, a compound described herein may be administered to the individual to detoxify the elevated ROS and free radicals already present in the blood and affected tissue or organ.

Alternatively, if the ischemic event is anticipated as in organ transplantation, then compounds described herein may be administered prophylactically, prior to the operation or ischemic event.

The compounds described herein may be used to treat any disease or condition associated with undesirable levels of ROS and free radicals, or to prevent any disease, disorder or condition caused by undesirable levels of ROS and free radicals. According to the invention, the compounds described herein may also be administered to provide a therapeutic or prophylactic treatment of elevated ROS and other free radicals associated with a variety of other diseases and conditions, including, but not limited to, oxygen toxicity in premature infants, burns and physical trauma to tissues and organs, septic shock, polytraumatous shock, head trauma, brain trauma, spinal cord injuries, Parkinson's disease, amyotrophic lateral sclerosis (ALS), Alzheimer's disease, age-related elevation of ROS and free radicals, senility, ulcerative colitis, human leukemia and other cancers, Down syndrome, arthritis, macular degeneration, schizophrenia, epilepsy, radiation damage (including UV-induced skin damage), and drug-induced increase in ROS and free radicals.

A progressive rise of oxidative stress due to the formation of ROS and free radicals also occurs during aging (see, e.g., Mecocci, P. et al., Free Radio. Biol. Med., 2000, 28: 1243-1248). This has been detected by finding an increase in the formation of lipid peroxidates in rat tissues (Erdincler, D. S., et al., Clin. Chim. Acta, 1997, 265: 77-84) and blood cells in elderly human patients (Congi, F., et al., Presse. Med., 1995, 24: 1115-1118). Accordingly, the compounds described herein, which are able to absorb peroxyl radicals, are also well suited for use in methods of preventing and/or counteracting increased tissue damage and decreased life expectancy due to elevated levels of ROS and free radicals that accompany the aging process.

Thus, the compounds of the invention have utility in the treatment of conditions and disorders caused by harmful reactive oxygen species (ROS) and other free radicals. Accordingly, the invention further relates to methods of increasing peroxyl radical absorbance in a tissue in a subject (e.g., a subject suffering from an ischemia), comprising administering to the subject an effective amount of a compound represented by Structural Formula I:

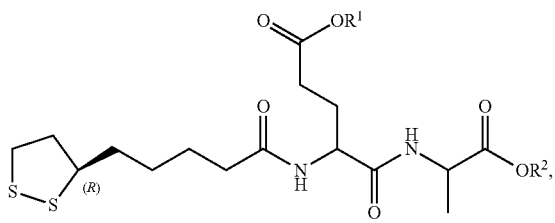

wherein R1 and R2 are each independently H or a hydrolyzable group, or a pharmaceutically acceptable salt thereof.

In a particular embodiment, the invention relates to a method of increasing peroxyl radical absorbance in a tissue in a subject, comprising administering to the subject an effective amount of a compound represented by Structural Formula II:

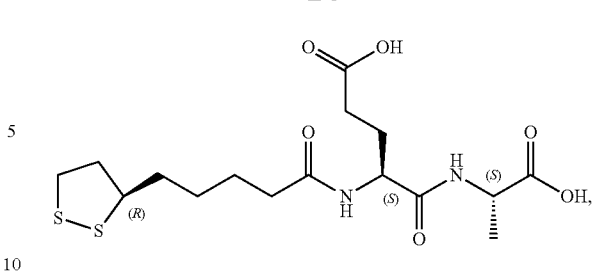

or a pharmaceutically acceptable salt thereof.

In another embodiment, the invention relates to a method of increasing peroxyl radical absorbance in a tissue in a subject, comprising administering to the subject an effective amount of a compound represented Structural Formula III:

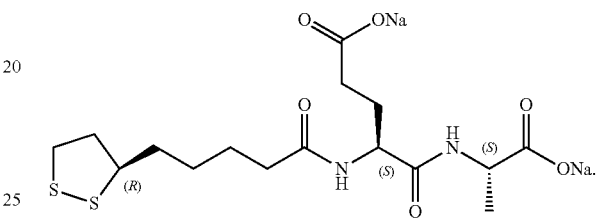

An exemplary assay for detecting peroxyl radical absorbance is described herein in Example 7. Other methods of detecting free radical absorbance are described in U.S. Pat. No. 6,890,896, the contents of which are incorporated herein by reference.

The activation of Akt kinase by a compound of the invention has utility in the treatment of conditions resulting from reduced or insufficient Akt activity in a cell, including, but not limited to, ischemic injuries. Suitable conditions resulting from reduced Akt activity for treatment using the compounds and methods of the invention include, for example, diseases or disorders characterized by insufficient vascularization (e.g., diabetic ulcers, gangrene, wounds requiring neovascularization to facilitate healing, Buerger's syndrome, hypertension, conditions characterized by a reduction in microvasculature), and certain neurological diseases or disorders (e.g., Parkinson's disease, Alzheimer's disease, depression, anxiety, manic-depressive psychosis, post traumatic stress disorder, mild cognition impairment (MCI), amyotrophic lateral sclerosis (ALS), Huntington's disease, spinocerebellar degenerative disease, multiple sclerosis (MS), Pick's disease, schizophrenia, anxiety neurosis, obsessive-compulsive neurosis, head trauma, spinal cord injury, cerebrovascular disorder, cerebrovascular dementia, asymptomatic brain infarction, polyglutamine disease, prion disease, corticobasal ganglionic degeneration, progressive supranuclear palsy, AIDS encephalopathy, muscular dystrophy, diabetic neuropathy).

Other conditions resulting from reduced Akt activity that may be treated using the compounds and methods of the invention include, but are not limited to, diabetic retinopathy, diabetic nephropathy, liver cirrhosis, alcoholic hepatitis, senile diseases characterized by a decrease in self-regenerating ability, non-metabolic bone diseases, metabolic bone diseases, joint diseases, periodontal diseases, cytomegalovirus infection, rheumatoid arthritis, Lyme disease, gout, sepsis syndrome, hyperthermia, ulcerative colitis, enterocolitis, osteoporosis, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic disease, asthma bronchiale, type I insulin dependent diabetes mellitus, arteriosclerosis, atherosclerosis, psoriasis, chronic B lymphocyte leukemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfusion syndrome, postsurgical inflammation, organ transplantation, and alopecia.

AKT-mediated disorders resulting from reduced AKT activity are also disclosed in US 2004/0122077; US 2006/0241168; and US 2007/0219139, the contents of which are incorporated herein by reference.

The pharmaceutical preparations disclosed herein are prepared in accordance with standard procedures and are administered at dosages that are selected to reduce, prevent, or eliminate, or to slow or halt the progression of, the condition being treated (See, e.g., Remington's Pharmaceutical Sciences, Mack Publishing Company, Easton, Pa., and Goodman and Gilman's The Pharmaceutical Basis of Therapeutics, McGraw-Hill, New York, N.Y., the contents of which are incorporated herein by reference, for a general description of the methods for administering various agents for human therapy). The compositions of a compound represented by the disclosed compounds can be delivered using controlled or sustained-release delivery systems (e.g., capsules, biodegradable matrices). Exemplary delayed-release delivery systems for drug delivery that would be suitable for administration of the compositions of the disclosed compounds are described in U.S. Pat. No. 5,990,092 (issued to Walsh); U.S. Pat. No. 5,039,660 (issued to Leonard); U.S. Pat. No. 4,452,775 (issued to Kent); and U.S. Pat. No. 3,854,480 (issued to Zaffaroni), the entire teachings of which are incorporated herein by reference.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. For example, the compounds of the present invention may be in powder form for reconstitution at the time of delivery. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing agents, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form. The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In general, the methods for delivering the disclosed compounds and pharmaceutical compositions of the invention in vivo utilize art-recognized protocols for delivering the agent with the only substantial procedural modification being the substitution of the compounds represented by any one of the disclosed compounds for the drugs in the art-recognized protocols.

The compounds of the present invention may be administered by any route, preferably in the form of a pharmaceutical composition adapted to such a route, and would be dependent on the condition being treated. The compounds and compositions may, for example, be administered intravascularly, intramuscularly, subcutaneously, intraperitoneally, orally or topically. It will be obvious to those skilled in the art that the following dosage forms may comprise as the active ingredient, either compounds or a corresponding pharmaceutically acceptable salt of a compound of the present invention. A preferred method of administration for the compounds of the invention is intravenous administration.

In some embodiments, the composition may be administered parenterally via injection. Parenteral administration can include, for example, intraarticular, intramuscular, intravenous, intraventricular, intraarterial, intrathecal, subcutaneous, or intraperitoneal administration. Formulations for parenteral administration may be in the form of aqueous or non-aqueous isotonic sterile injection solutions or suspensions. These solutions or suspensions may be prepared from sterile powders or granules having one or more of the carriers mentioned for use in the formulations for oral administration. The compounds may be dissolved in polyethylene glycol, propylene glycol, ethanol, corn oil, benzyl alcohol, sodium chloride, and/or various buffers (e.g., sodium bicarbonate, sodium hydroxide).

For oral administration, the pharmaceutical compositions may be in the form of, for example, a tablet, capsule, suspension or liquid. The composition is preferably made in the form of a dosage unit containing a therapeutically effective amount of the active ingredient. Examples of such dosage units are tablets and capsules. For therapeutic purposes, the tablets and capsules can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example potato starch, flavoring or coloring agents, or acceptable wetting agents. Oral liquid preparations generally in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For topical use the compounds of the present invention may also be prepared in suitable forms to be applied to the skin, or mucus membranes of the nose and throat, and may take the form of creams, ointments, liquid sprays or inhalants, lozenges, or throat paints. Such topical formulations further can include chemical compounds such as dimethylsulfoxide (DMSO) to facilitate surface penetration of the active ingredient. Suitable carriers for topical administration include oil-in-water or water-in-oil emulsions using mineral oils, petrolatum and the like, as well as gels such as hydrogel. Alternative topical formulations include shampoo preparations, oral pastes and mouthwash.

For application to the eyes or ears, the compounds of the present invention may be presented in liquid or semi-liquid form formulated in hydrophobic or hydrophilic bases as ointments, creams, lotions, paints or powders.

For rectal administration the compounds of the present invention may be administered in the form of suppositories admixed with conventional carriers such as cocoa butter, wax or other glyceride. For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Delivery can also be by injection into the brain or body cavity of a patient or by use of a timed release or sustained release matrix delivery systems, or by onsite delivery using micelles, gels and liposomes. Nebulizing devices, powder inhalers, and aerosolized solutions are representative of methods that may be used to administer such preparations to the respiratory tract. Delivery can be in vitro, in vivo, or ex vivo.

For example, suitable dosages for a compound of the invention can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage for a particular agent, patient and ischemia or ischemia-reperfusion injury is well within the abilities of one of skill in the art. Preferably, the dosage does not cause or produces minimal adverse side effects.

A therapeutically effective amount of a compound of the invention can be administered alone, or in combination with one or more other therapeutic agents. Suitable therapeutic agents that are useful for treating ischemic injuries, which can be administered in combination with a compound of the invention, include, but are not limited to, calcium channel blockers, beta blockers, nitroglycerin, aspirin, anti-inflammatory agents, natriuretic factors, vasodilators, thrombolytic and antithrombolic agents.

Thus, a compound of the invention can be administered as part of a combination therapy (e.g., with one or more other therapeutic agents). The compound of the invention can be administered before, after or concurrently with one or more other therapeutic agents. In some embodiments, a compound of the invention and other therapeutic agent can be co-administered simultaneously (e.g., concurrently) as either separate formulations or as a joint formulation. Alternatively, the agents can be administered sequentially, as separate compositions, within an appropriate time frame, as determined by the skilled clinician (e.g., a time sufficient to allow an overlap of the pharmaceutical effects of the therapies). A compound of the invention and one or more other therapeutic agents can be administered in a single dose or in multiple doses, in an order and on a schedule suitable to achieve a desired therapeutic effect (e.g., a reduction in and/or inhibition of joint inflammation). Suitable dosages and regimens of administration can be determined by a clinician and are dependent on the agent(s) chosen, pharmaceutical formulation and route of administration, various patient factors and other considerations.

EXAMPLES

Example 1

Synthesis of Compounds

Materials and Methods:
Synthesis of RLip-EA-OH (Lip-EA)
RLipoic Acid (RLip-OH, 1.00 g) was dissolved in dioxane. The solution was protected from direct light by covering the reaction flask with foil. DIEA (0.845 mL) and DSC (1.24 g) were added sequentially and the reaction was stirred vented overnight at room temperature to form Lip-NHS in situ. An aqueous solution of glutamyl-alanine (H-EA-OH, 1.11 g) and DIEA (2.65 mL) was prepared and added to the solution of Lip-NHS. The combined solution was stirred overnight and then transferred to a reparatory funnel. Ethyl acetate followed by 5% KHSO4 (aq) was added to the reaction mixture. The organic phase was collected and washed with 5% KHSO4 (aq) followed by saturated NaCl (aq). The organic phase was again collected, dried with anhydrous Na2SO4 and after filtration evaporated in vacuo to yield crude RLip-EA-OH as a light yellow foam. A portion of the crude foam was dissolved for purification by RP-HPLC with 2:1 water-acetonitrile (0.5% HOAc) and the product isolated on a YMC Pack Pro C18 reverse phase column using a gradient of increasing acetonitrile (0.5% acetic acid) in water (0.5% acetic acid). Product containing fractions were identified by analytical HPLC, pooled, frozen, and lyophilized to provide RLip-EA-OH (165 mg) at 100% HPLC purity (area % at 220 nm). The product NMR was consistent with structure and had an observed mass of 405 (M-1), calculated 406.

R/SLip-EA-OH, and SLip-EA-OH were prepared using a similar procedure. Optically pure RLip-OH and SLip-OH starting materials were obtained for the preparation of RLip-EA-OH and SLip-EA-OH, respectively. Optical purity was assayed by optical rotation and met release specifications. Product structure and identity was confirmed by MS, HPLC retention time shift (relation to Lip-OH starting material) and in most cases NMR. Compound structures, names, and appropriate abbreviations for the compounds described herein are contained in Table 1. Analytical data on the compounds described in this Example are shown in Table 2.

RLip-OH was obtained commercially (Labochim, Milan, Italy). R/SLip-Ea-OH and Ac-EA-OH were obtained by contract.

Preparation of the Dilysine Salt of RLip-EA-OH (Lip-EA)
RLip-EA-OH (20.0 g) was dissolved in ethanol water (19:1). Two equivalents of lysine (14.4 g) were added to the ethanolic solution of RLip-EA-OH and the slurry was warmed to reflux. After refluxing for 30 minutes, the solution was allowed to cool to room temperature. The product dilysine salt of RLip-EA-OH was recovered by filtration, rinsed with absolute ethanol and dried to a constant weight for a 96% recovery of dilysine salt of RLip-EA-OH.

TABLE 1

Compound Abbreviations, Structures, and Chemical Names.

| Compound Abbreviations | Compound Structure | Full Name* |
|---|---|---|
| RLip-OH | 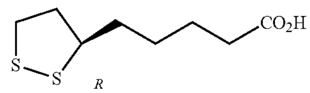 | (R)-lipoic acid |
| RLip-LGlu-LAla-OH; RLip-EA-OH | 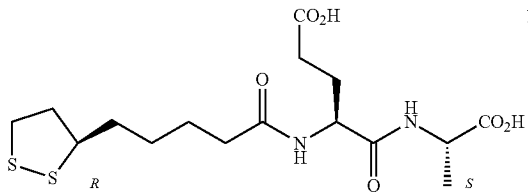 | N-(R)-lipoyl-L-glutamyl-L-alanine |
| R/SLip-LGlu-LAla-OH; R/SLip-EA-OH | 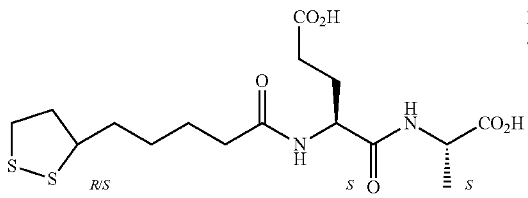 | N-(R/S)-lipoyl-L-glutamyl-L-alanine |
| SLip-LGlu-LAla-OH; SLip-EA-OH | 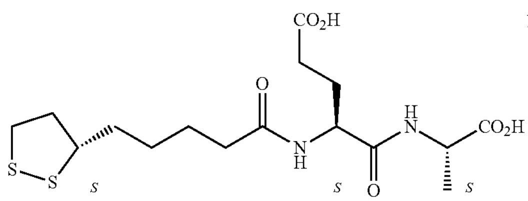 | N-(S)-lipoyl-L-glutamyl-L-alanine |
| R/SLip-LGlu-DAla-OH; R/SLip-Ea-OH | 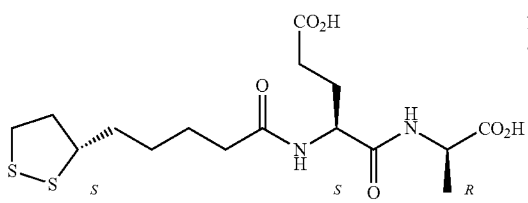 | N-(R/S)-lipoyl-L-glutamyl-D-alanine |
| Ac-LGlu-LAla-OH; Ac-EA-OH | 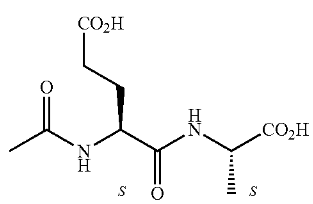 | N-acetyl-L-glutamyl-L-alanine |

*Standard nomenclature was used for natural amino acids and common analogs [*J. Biol. Chem.* 1972, 247:977-983]; Lipoyl = 1,2-dithiolane-3-pentanoyl

TABLE 2

Analytical Data for Compounds Listed in Table 1.

| Compound | NMR* | HPLC Purity[#] | Mass Spectroscopy | Optical Rotation |
|---|---|---|---|---|
| RLip-OH[†] | NA | 99.9% | NA | +121.7 |
| RLip-LGlu-LAla-OH | Dithiolane —CH—S— m, 1H, δ 3.10 Glutamyl, Alaninyl αC—H m, 2H, δ 4.38 | 100% | Calc: 406 Found (M − 1): 405 | +36.1 |
| R/SLip-LGlu-LAla-OH[†] | Dithiolane —CH—S— m, 1H, δ 3.10 Glutamyl, Alaninyl αC—H m, 2H, δ 4.38 | 99.6% | Calc: 406 Found: 406 | −24.2 |
| SLip-LGlu-LAla-OH | NA | 96.5% | Calc: 406 Found (M − 1): 405 | −69.5 |

TABLE 2-continued

Analytical Data for Compounds Listed in Table 1.

| Compound | NMR* | HPLC Purity# | Mass Spectroscopy | Optical Rotation |
|---|---|---|---|---|
| R/SLip-LGlu-DAla-OH† | NA | 99.6% | Calc: 406<br>Found: 406 | NA |
| Ac-LGlu-LAla-OH† | NA | 99.6% | Calc: 261<br>Found: 261 | NA |

*$^1$H NMR obtained in either Methanol ($d_4$) or DMSO ($d_6$)
Area percent at $\lambda = 220$ nm
†Purchased commercially or via contract, analytical data from certificate of analysis.
NA = not available Example 2

RLip-EA-OH Treatment Induces Akt Phosphorylation/Activation in a Dose Dependent Manner in Cultured Cells Aid is activated via phosphorylation by activation of signal transduction pathways through known receptors in the plasma membrane of cells. Phosphorylated Akt is readily detected with specific antibodies in situ in fixed and permeabilized cells.

Materials and Methods:

Cytoblot Assay for Akt Activation

The ability of RLip-EA-OH to increase phosphorylated Akt was assayed using an in-cell western blot, or cytoblot. A549 cells (human non-small cell lung cancer cell line) were selected because these cells can be manipulated to increase or decrease the level of phosphoryated Akt. The cells were inoculated onto culture plates and allowed to adhere to the bottom, then treated, fixed, and permeabilized. Following permeabilization, the cells were treated with antibodies specific for either phospho-Akt or total Akt. The cells were then treated with fluorescent secondary antibodies to quantify the amount of bound primary antibody. Total Akt and phospho-Akt were simultaneously detected.

A549 cells were plated in 384 well black-wall, clear-bottom, cell culture-treated microtiter plates at 70% confluence. Cells were incubated overnight to allow cell attachment. The media was changed to low serum (0.1%, fetal bovine serum [FBS]) and the cells were incubated for another 24 hours. Cells were treated with test compounds, fixed and permeabilized for the Akt assay. The fixative was 3.7% formaldehyde in phosphate buffered saline. The permeabilization buffer was 0.5% Triton X-100 in phosphate buffered saline. After permeabilization of cells, the amounts of total Akt and phosphorylated Akt at either of the two phosphorylation sites (threonine-308 and serine-473) were determined at 7 test concentrations, each performed in quadruplicate. The phospho-Akt data were normalized to total Akt and background subtracted for analysis.

Following overnight serum starvation to reduce basal Akt phosphorylation, cells were stimulated with vehicle, RLip-EA-OH, or RLip-OH. Cells were treated for 45 minutes or 3 hours and studied for phosphorylation at serine-473 or threonine 308, respectively.

Immunohistochemistry Assay for Phosphorylated Akt

The ability of RLip-EA-OH to increase phosphorylated Akt was assayed in H9c2 cells by immunocytochemistry followed by visualization using microscopy. H9c2 cells are a cell line derived from rat cardiac myocytes and can be manipulated to increase or decrease the level of phosphoryated Akt. Cells were inoculated onto culture plates and allowed to adhere to the bottom, treated, fixed, and permeabilized. Following permeabilization, cells were treated initially with specific phospho-Akt antibodies followed by fluorescent secondary antibodies to quantify the amount of bound primary antibody.

H9c2 cells were plated in 12 well cell culture treated plates at 70% confluence. Cells were incubated overnight to allow cell attachment. The media was changed to low serum (0.5%, fetal bovine serum [FBS]) and cells incubated for another 48 hours. Cells were treated for 3 hours with either vehicle, RLip-EA-OH (50 µM), or co-treatment with LY294002 (25 µM), fixed with 3.7% formaldehyde in phosphate buffered saline and permeabilized with 0.5% Triton X-100 in phosphate buffered saline. After permeabilization, the cells were treated with antibody specific for Akt phosphorylated at threonine-308, followed by treatment with a fluorescent labeled secondary antibody.

Figure 2:
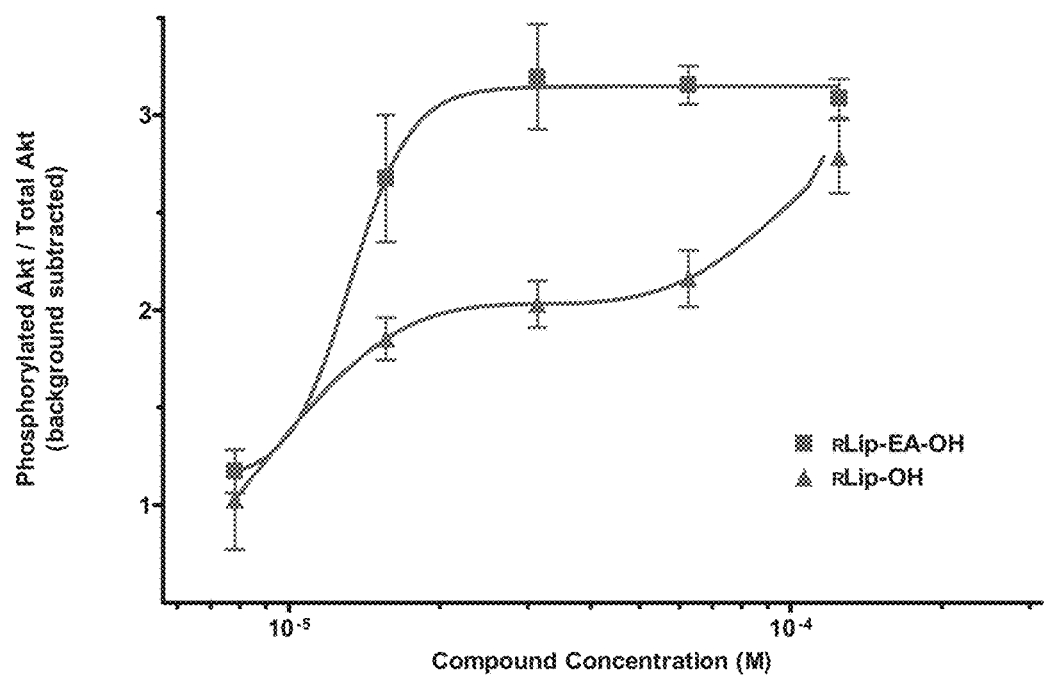
FIG. 2 is a graph depicting the effect of RLip-EA-OH and RLip-OH at variant concentrations on the level of Akt phosphorylation in A549 cells. Data is presented as the mean±sem (N=4) of the background subtracted ratio of phosphorylated Akt to total Akt.

Result:

The effect of RLip-EA-OH and RLip-OH on Akt phosphorylation relative to total Akt was assessed in A549 cells using a cytoblot assay as described. A 3-fold and 2-fold increase in phosphorylated Akt at serine 473 was observed following 45 minutes of treatment with RLip-EA-OH and RLip-OH, respectively (FIG. 2). Both RLip-EA-OH and RLip-OH increased the amount of phosphorylated Akt relative to total Akt in a dose dependent manner. RLip-EA-OH was more effective than RLip-OH at most dose levels.

Figure 3:
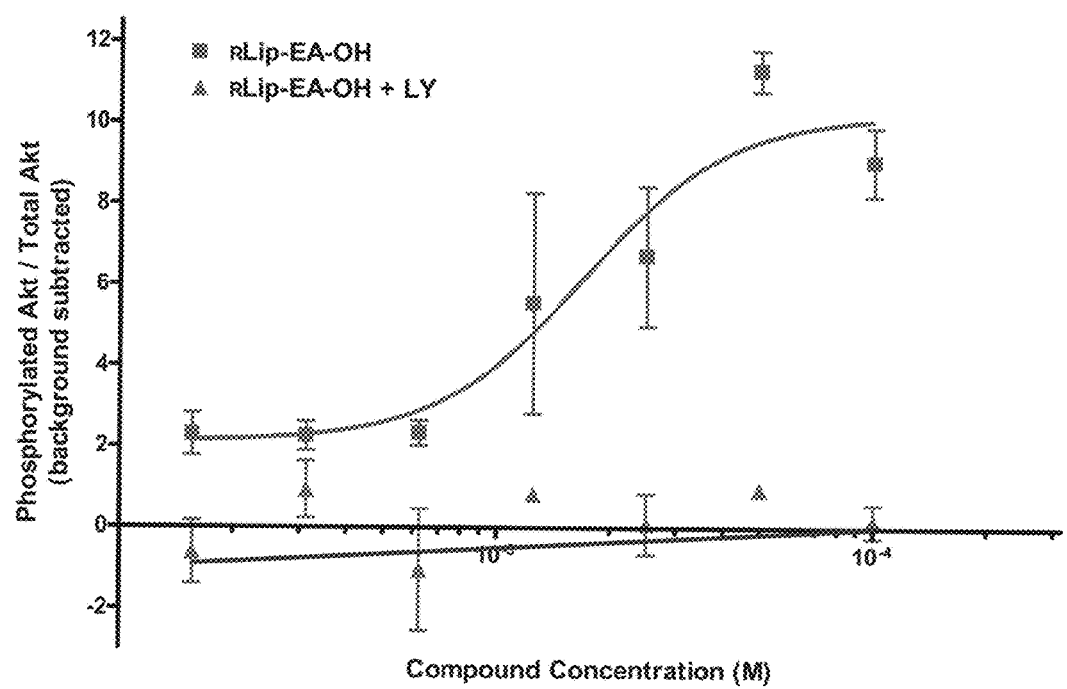
FIG. 3 is a graph depicting the effect of RLip-EA-OH at variant concentrations on the level of Akt phosphorylation in A549 cells alone or in the presence of LY294002, a known phosphotidylinositol-3'-kinase inhibitor. Data is presented as the mean±sem (N=4) of the background subtracted ratio of phosphorylated Akt to total Akt.

RLip-EA-OH treatment in the presence and absence of LY294002, a known phosphotidylinositol-3'-kinase inhibitor (Vlahos, C. J., Matter, W. F., Hui, K. Y., Brown, R. F. A specific inhibitor of phosphatidylinositol 3-kinase, 2-(4-morpholinyl)-8-phenyl-4H-1-benzopyran-4-one (LY294002). J Biol Chem 1994, 269:5241-5248), was also evaluated. Cells were treated for 3 hours and studied for phosphorylation at tyrosine-308. Increased Akt phosporylation was observed following 3 hours of treatment with RLip-EA-OH alone. The increased phosphorylation of Akt in response to RLip-EA-OH treatment was completely inhibited by cotreatment with 5 µM LY294002 (FIG. 3).

In addition, the effect of RLip-EA-OH on Akt phosphorylation was assessed in H9c2 cells using an immunohistochemistry assay as described. RLip-EA-OH treatment was compared to either vehicle treatment or RLip-EA-OH treatment in the presence of LY294002. Cells treated with vehicle showed little fluorescence. Fluorescence intensity was much brighter in cells that were treated for 3 hours with RLip-EA-OH. Co-treatment of cells with LY294002 for an additional 30 minutes prior to the addition of RLip-EA-OH diminished the fluorescence intensity from Akt phosphorylation.

Example 3

RLip-EA-OH Activates Insulin Receptor Tyrosine Kinase (IRK)

Materials and Methods: IRK Activation Assay

Insulin receptor kinase activity was readily measured by a mobility shift assay using a Caliper LabChip® 3000 and a 12-sipper LabChip® to detect both phosphorylated and unphosphorylated substrate (Caliper Life Sciences, Discovery Alliances and Services Division, Hanover, Md.). The mobility-shift kinase assay uses a microfluidic chip to measure the conversion of a fluorescent peptide substrate to a phosphorylated product. The reaction mixture from a microtiter plate well was introduced through a capillary sipper onto the chip and the nonphosphorylated substrate and phosphorylated product were separated by electrophoresis and detected via laser-induced fluorescence. The signature of the fluorescence signal over time revealed the extent of the reaction. The catalytic subunits of tyrosine kinases have endogenous levels of activity in the presence of ATP and substrate, thus the results are presented as a % of control.

Specifically, each test compound was diluted to 25 times its assay concentration with 100% DMSO and added to 12 μL of an assay buffer solution (100 mM HEPES, 10 mM MnCl2, 5 mM B-GP, and 0.002% Brij) containing dithiotheritol (DTT, 2 mM) and insulin receptor kinase domain (Millipore catalog #14-466, 80 nM) prior to pre-incubation at room temperature for 15 minutes. Following the pre-incubation, assay buffer (12 μL) containing 304 of a fluorescent peptide substrate and ATP (162004) was added and the mixture further incubated at room temperature for an additional 1.5 hours at which point approximately 50% of the substrate was converted to product. The samples were placed on the LabChip 3000 to measure the amount of parent substrate and phosphorylated product.

Results:

Using the IRK activation assay described above, compounds were evaluated at 100 μM for their ability to activate the insulin receptor tyrosine kinase (IRK). The results of this assay are shown in Table 3.

TABLE 3

The Effect of Compounds at 100 μM on the Activity of the Insulin Receptor Kinase.

| Compound | AVG % activity above control (±SEM) |
|---|---|
| RLip-EA-OH | 78 ± 15 |
| R/SLip-EA-OH | 14 ± 1 |
| SLip-EA-OH | 4 ± 12 |
| R/SLip-Ea-OH | 1 ± 6 |

Example 4 rLip-EA-OH Activates IGF1R Kinase and Src Tyrosine Kinase

Materials and Methods: IGF1 and Src Tyrosine Kinase Activation Assay.

IGF1R and Src tyrosine kinases have endogenous levels of activity in the presence of ATP and substrate. This activity was readily measured using a mobility shift assay using a Caliper LabChip® 3000 and a 12-sipper LabChip® to detect both phosphorylated and unphosphorylated substrate (Caliper Life Sciences, Discovery Alliances and Services Division). Enzyme, substrate and ATP concentrations were optimized for each assay. For the IGF1R assay, the final concentrations of the enzyme, peptide and ATP were 20 nM, 1.5 μM, and 1220 μM, respectively. For the Src assay, the final concentrations of the enzyme, peptide and ATP were 2.5 nM, 1.5 μM, and 17 μM, respectively.

RLip-EA-OH was evaluated at multiple concentrations for an effect on activation of IGF1 receptor kinase (IGF1R) and Src. The effects of a 100 μM concentration of different Lip-EA compounds on kinase activation are shown in Table 4a. The compounds tested activated IGF1R and Src with different selectivities.

The effect of 300 μM RLip-EA-OH or RLip-OH on activation of different tyrosine kinases was also assessed (Table 4b). At this concentration, RLip-EA-OH induced a significantly greater activation of both IRK and Src tyrosine kinases than RLip-OH, relative to vehicle control.

TABLE 4a

The Effect of Compounds at 100 μM on the Activity of IGF1R and Src kinases.

| Compound | IGF1R % activity above control (±SEM) | Src % activity above control (±SEM) |
|---|---|---|
| RLip-EA-OH | 42 ± 1 | 70 ± 1 |
| R/SLip-EA-OH | 27 ± 3 | 43 ± 1 |
| R/SLip-Ea-OH | 17 ± 12 | 29 ± 1 |
| SLip-EA-OH | −4 ± 10 | 19 ± 1 |

TABLE 4b

The Effect of RLip-EA-OH and RLip-OH at 300 μM on the activity of IRK, IGF1R and Src Tyrosine Kinases. The data are the % increase in activity above vehicle control.

| | % Increase in activity at 300 μM | |
|---|---|---|
| Tyrosine Kinase | RLip-EA-OH | R-α-Lip-OH |
| IRK | 77 ± 7 | 48 ± 1 |
| IGF1R | 33 ± 3 | 37 ± 4 |
| Src | 78 ± 2 | 15 ± 1 |

Example 5 rLip-EA-OH Prevents Apoptosis and Promotes Cell Survival in Cultured Cells

Materials and Methods: Cell Survival Assay in Jurkat Cells

The ability of rLip-EA-OH to prevent apoptosis and promote cell survival was assessed using Jurkat cells deficient in Receptor-Interacting Protein (RIP), a cell death mediating protein. The Jurkat cell line is derived from human T-Lymphocytes. RIP-deficient Jurkat cells are susceptible to apoptosis when treated with tumor necrosis factor alpha (TNFα). These cells were treated with either vehicle or rLip-EA-OH and then apoptosis was triggered with TNFα. Cell survival was assessed to evaluate if rLip-EA-OH protected the cells against TNFα induced apoptosis.

RIP-deficient Jurkat cells were seeded into 96 well plates at 20,000 cells per well and treated for 2 hours with rLip-EA-OH (6 wells for each concentration) or DMSO. After pretreatment, 3 wells for each dose of drug were exposed to 10 ng/mL human recombinant TNFα (TNFα was not added to the other 3 wells). Twenty four hours after TNFα treatment, ATP cell viability was determined (Cell-Titer-Glo, Promega) and the values were used to calculate % survival of the cells.

In the absence of RLip-EA-OH, approximately 20% of the cells did not survive TNFα treatment. Treatment of cells with RLip-EA-OH prevented TNFα induced cell death in a dose dependent manner (Table 5).

TABLE 5

The effect of RLip-EA-OH on TNFα-induced apoptosis in RIP-deficient Jurkat cells.

| | RLip-EA-OH (µM) | | | | | | |
|---|---|---|---|---|---|---|---|
| | 0* | 0.006 | 0.012 | 0.05 | 0.1 | 0.2 | 1.5 |
| % Survival (%) | 82 | 84 | 95 | 96 | 98 | 101 | 106 |
| SD | 0.1 | 3 | 7 | 5 | 3 | 6 | 3 |

*Control

Example 6

RLip-EA-OH Inhibits Carbachol-Stimulated Increases in Intracellular Calcium in a Dose-Dependent Manner in Cultured Cells Materials and Methods: Cytosolic Calcium Overload Assay Cytosolic calcium increases in the CHO M1-WT3 cells when stimulated with carbachol ([Molecular Devices, Flex-Station Application Note 2, Comparison of FLIPR® and FLEXstation™ for Calcium Mobilization Assays]) and may be detected with a fluorescent dye that binds calcium. An increase in fluorescence following carbachol stimulation is interpreted as an increase in cytosolic calcium. Chinese hamster ovary (CHO) cells were allowed to adhere to the bottom of a 96-well culture plate. The fluorescent dye and a test sample were placed on the plate and allowed to be taken up by the cells. The fluorescence level was measured every two seconds using a plate reader (Flexstation II, Molecular Devices, Sunnyvale Calif.). The cells were stimulated with carbachol and flourescent data reported as the peak increase in fluorescence above baseline following carbachol stimulation. Data were normalized to the peak carbachol response in the control sample.

CHO cells from the cell line CHO-M1-WT3 were grown in Hams F12 medium supplemented with 10% FBS and 5 µg/mL G418 to maintain expression of the M1 muscarinic receptor. Cells were seeded the night before the experiment at a concentration of 30,000 cells/well in a volume of 100 µL per well of black walled, clear bottomed, 96-well microplates ("assay plates"). Cells were incubated at 37° C. and 5% $CO_2$ overnight. The next day, the cells were incubated at 37° C. for 60 minutes with Fluo-4 NW or Calcium-3 in Hank's Balanced Salt Solution along with 2.5 mM water soluble probenecid and the test compound at the indicated concentrations or vehicle. The final volume in each well was 200 µL. The cells were placed into the FlexStation system to monitor fluorescence before and after the addition of 50 µL of 1 µM carbachol for a final concentration of 200 nM. Fluorescence was measured for 17 seconds prior to carbachol addition and 43 seconds following carbachol addition. The Fluo-4 dye was excited at a wavelength of 485 nm and emission measured at 525 nm. The Calcium-3 dye was excited at a wavelength of 494 nm and emission measured at 525 nm. The calcium response was reported as the peak fluorescence minus the baseline fluorescence calculated as the average of the fluorescence prior to carbachol addition.

Figure 4:
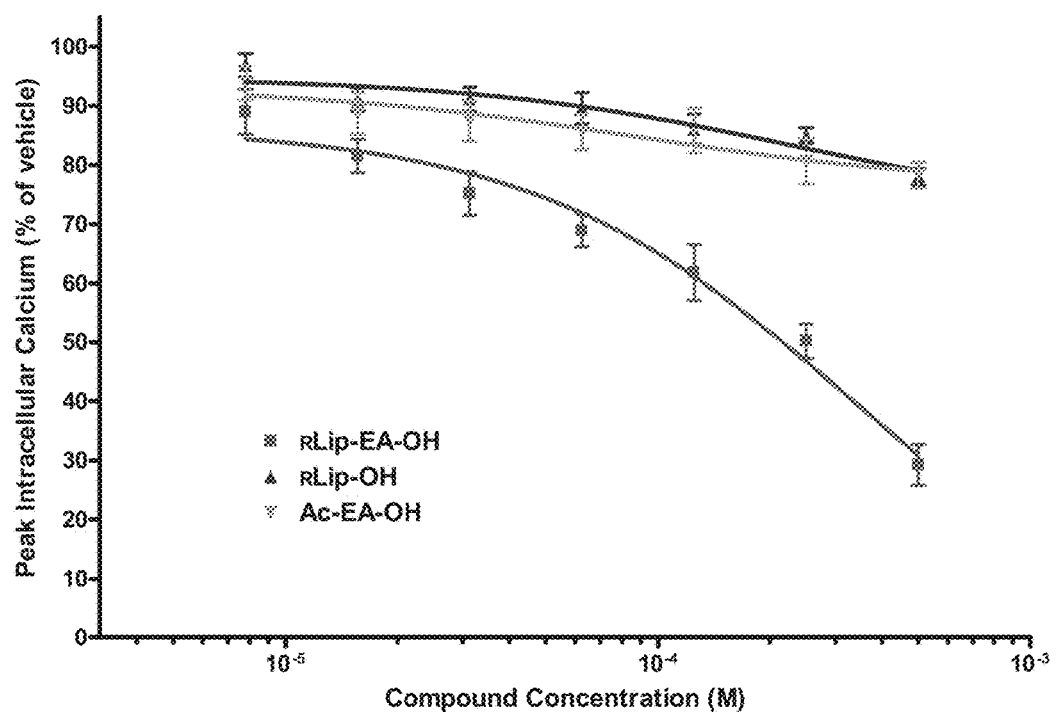
FIG. 4 is a graph depicting the effect at variant concentrations of RLip-EA-OH, Ac-EA-OH and RLip-OH on calcium flux in Chinese hamster ovary (CHO) cells. Data is presented as the mean±sem (N=4) measuring cytosolic calcium levels as a percentage of a buffer-only control.

Result:

The ability of RLip-EA-OH, RLip-OH and Ac-EA-OH to prevent calcium overload in CHO M1-WT3 cells was determined. The peak rise in cytosolic calcium of CHO cells expressing muscarinic M1 receptor was measured in response to carbachol stimulation. RLip-EA-OH diminished the flux in cytosolic calcium in a dose dependent manner, whereas RLip-OH and Ac-EA-OH had minimal effect (FIG. 4). RLip-EA-OH has an inhibitory effect on carbachol stimulated increases in cytosolic calcium and the inhibition is dose dependent. RLip-OH and Ac-EA-OH had only modest cytosolic calcium diminishing activity.

Example 7

RLip-EA-OH Demonstrates a Greater Peroxyl Radical Absorbance Capacity than RLip-OH Materials and Methods: Oxygen Radical Absorbance Capacity (ORAC) Assay Peroxyl radicals are one species of reactive oxygen produced by cells during reperfusion. The presence of peroxyl radicals can be detected by fluorescein oxidation. In the presence of peroxyl radicals, fluorescein fluorescence will decay over time. In the presence of an oxygen radical scavenger, the rate of decay is diminished. The change in the rate of decay between control and in the presence of scavengers is used to measure the peroxyl radical scavenging ability of a test compound.

Each compound tested was diluted to a concentration ranging from 25 µM to 250 µM in 10 mM phosphate buffer (pH=7.4) containing 10 nM fluorescein. The buffer and compound were incubated at 37° C. for 10 minutes. After the incubation, flourescein fluorescence was measured using a plate reader (Molecular Devices Flexstation II, Ex=485, Em=520). Baseline fluorescence measurements were recorded for 15 minutes before 2,2'-azobis(2-methylpropionamidine) dihydrochloride (AAPH) was added. The fluorescence decay was recorded for 90 minutes. The fluorescence decay without compound was subtracted from the fluorescence decay with compound. The slope of the decay vs. concentration is reported as the absorbance capacity.

Results:

The peroxyl radical absorbance capacity for lipoyl-containing compounds was determined (Tables 6a and 6b). RLip-EA-OH displayed a greater peroxyl radical absorbance capacity than RLip-OH. The results also indicate that the-lipoyl moiety is critical for scavenging peroxyl radicals in the ORAC assay, as acetyl-glutamylalanine had no appreciable peroxyl radical absorption capability.

TABLE 6a

ORAC assay results relative to RLip-OH.

| Compound | ORAC Value |
|---|---|
| RLip-OH | 100 ± 6 * |
| RLip-EA-OH | 131 ± 6 |
| Ac-EA-OH | 8 ± 5 † |

Values are the mean of 3-4 experiments.

TABLE 6b

ORAC assay results relative to RLip-EA-OH

| Compound | ORAC Value |
|---|---|
| RLip-EA-OH | 100 ± 11 |
| R/SLip-EA-OH | 102 ± 10 |
| SLip-EA-OH | 89 ± 4 |

Values are the mean of 3-4 experiments.

Example 8 rLip-EA-OH Protects the Myocardium Against Ischemia-Reperfusion Injury In Vivo

Materials and Methods: Rat Model of MI/R Injury

A rat model of MI/R injury was used as an in vivo screen to determine if certain lipoic acid derivative compounds are cardio-protective (e.g., against mycoardial ischemia-reperfusion injury). This model is analogous to the ischemia-reperfusion injury observed in cardiac patients following coronary occlusions and cardiac surgery procedures, such as coronary artery bypass grafting (CABG) (Matsui, T., Tao, J., del Monte, F., Lee, K.-H. et al., Akt Activation Preserves Cardiac Function and Prevents Injury After Transient Cardiac Ischemia In vivo, *Circulation* 2001, 104:330).

General Procedure

The circumflex branch of the left coronary artery was ligated temporarily to induce regional ischemia in the left ventricular mass, followed by the injection of fluorescent microspheres to delineate the ischemic region. The animals were sacrificed about 24 hours after reperfusion and the hearts were excised, sectioned and stained with triphenyltetrazolium. The direct impact of the pharmacologic intervention was determined by measuring the myocardial infarct area (MI), the ischemic area at risk (AR) and the left ventricular area (LV). The reduction of MI over the AR (MI/AR ratio) was used as the primary measure of drug efficacy relative to vehicle controls.

Detailed Procedure

Male Sprague-Dawley rats between 300 and 350 gm were used for these experiments. Anesthesia was induced with 3-4% isoflurane in an induction chamber. After induction, anesthesia was maintained at a surgical plane with 1.5-2.0% isoflurane, administered by a Rodent Ventilator through a 16-gauge angiocatheter introduced orally into the trachea. The ventilator was set at 2.5 cc at a rate of 60-65 breaths per minute to maintain ventilation during surgery. The core temperature of the animal was monitored and maintained at 37° C. using a rectal probe and a heating lamp attached to a temperature controller.

A left anterior thoracotomy was performed and the heart was exposed using a vertical pericardotomy. The circumflex branch of the left coronary artery (LCx) was ligated approximately 4 mm from the aorta using a cardiovascular 7.0 monofilament suture on an 11 mm needle to induce ischemia in the left ventricle.

Fluorescent microspheres (300 μL) were injected into the left ventricular cavity 10-20 minutes after the ligation to delineate the ischemic area. The suture was removed 30 minutes after ligation to reperfuse the ischemic area and the ischemic area was checked for reperfusion.

The chest was then closed in layers using absorbable suture (Dexon 5-0) for the muscle layers and monofilament Nylon 5-0 suture was used to close the cutaneous layer. The animals were allowed to recover, then were returned to the colony.

Twenty-four hours after reperfusion, anesthesia was induced using ketamine hydrochloride and the chest was opened. The animals were sacrificed with 15% potassium chloride aqueous solution (w/v) injected into the LV cavity to arrest the heart in diastole. The heart was excised distal to the aortic valve and washed with saline to remove the blood. Sagittal slices of the heart were obtained between the base of the ventricle and the apex. Five slices of heart tissue were obtained, each 2 mm thick. The slices were immersed in a 1% 2,3,5-triphenyl-2H-tetrazolium chloride (TTC) in saline solution and then stored in the dark for 30 minutes to stain.

Images of the slices were obtained under bright field (to observe the TTC staining) and under fluorescence (to observe the microspheres). The area at risk was determined by the absence of microspheres and the infarct area was determined by the absence of TTC staining.

Figure 5:
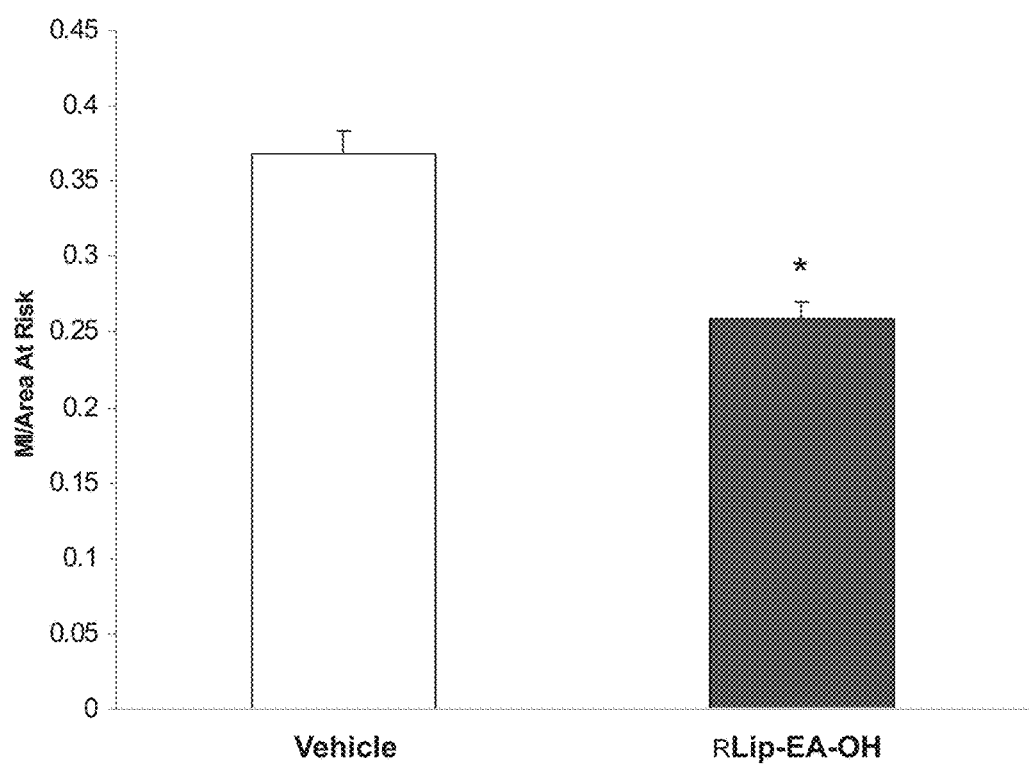
FIG. 5 is a graph depicting the efficacy of RLip-EA-OH in a rat model of myocardial ischemia-reperfusion injury. Data is presented as the ratio of myocardial infarct size divided by the total area at risk (MI/AR). The results represent a meta analysis of animals treated via an intracardial injection with RLip-EA-OH at 1 mg/kg (N=64) vs. saline vehicle (N=54). Animals treated with RLip-EA-OH had significantly (p<0.001) reduced (33%) infarct area (dead tissue) to area at risk ratio compared to those animals receiving saline vehicle.

Result:

A meta analysis of rLip-EA-OH treated animals (n=64) vs. saline vehicle-treated (n=54) animals in the myocardial ischemia-reperfusion model demonstrated that rLip-EA-OH administered as an intraventricular cavity injection (1 mg/kg IC), effectively reduced the myocardial infarct (MI) size relative to the area at risk (AR). The MI:AR ratios for vehicle and rLip-EA-OH treated animals were 0.373 (n=54) and 0.250 (n=64), respectively corresponding to a 33% difference between groups (p<0.001)(FIG. 5). A significant reduction in the area of cardiac damage was observed in myocardial tissue sections following rLip-EA-OH treatment.

Figure 6:
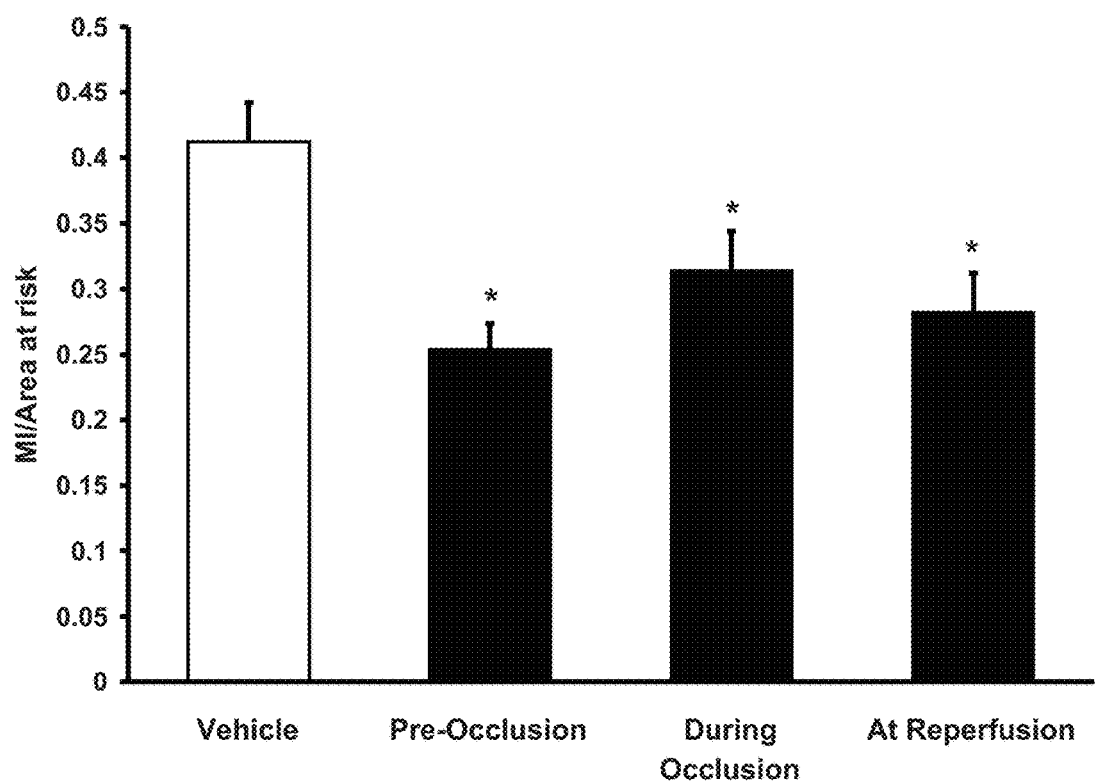
FIG. 6 is a graph depicting the effect of timing of intracardial administration of RLip-EA-OH at 1 mg/mL on reduction of myocardial damage in a rat model of cardiac ischemia-reperfusion injury. Data is presented as the ratio of myocardial infarct size divided by the total area at risk (MI/AR) and displayed as the mean±sem (N=12-15/group). Results indicate that treatment with RLip-EA-OH significantly ($p<0.05$) reduced myocardial tissue death when administered 15 min pre-occlusion (pre-occlusion, 38%), 15 min after occluding (during occlusion, 24%), and within 1 min after reperfusion (at reperfusion, 32%) compared to those animals receiving saline vehicle 15 min pre-occlusion.
Figure 7:
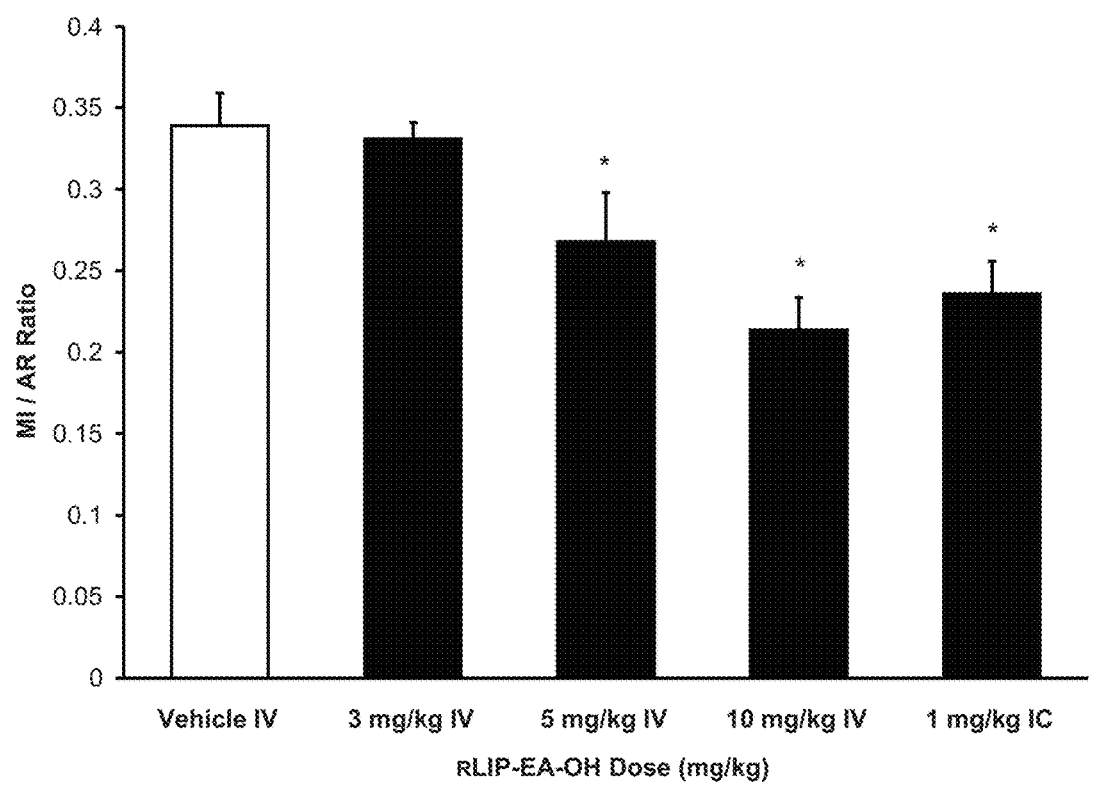
FIG. 7 is a graph depicting the effect of different doses of RLip-EA-OH in a rat model of myocardial ischemia-reperfusion injury. RLip-EA-OH was administered 15 minutes pre-occlusion by intravenous (IV) or intra left ventricular cardiac (IC) administration. Data is presented as the ratio of myocardial infarct size divided by the total area at risk (MI/AR) and displayed as the mean±sem (N=10-12/group). Results indicate that treatment with RLip-EA-OH significantly ($p<0.05$) reduced myocardial tissue death and was dose dependent.

The timing of administration of rLip-EA-OH was investigated in the rat myocardial ischemia-reperfusion model. rLip-EA-OH was administered at 1 mg/kg IC pre-ischemia (15 minutes pre-occlusion), intra-ischemia (15 minutes after occluding), or post-ischemia (within 1 minute after reperfusion). rLip-EA-OH significantly (p<0.05) reduced myocardial tissue death pre-occlusion (38%), during occlusion (24%), and at reperfusion (32%) compared to those animals receiving saline vehicle (FIG. 6). rLip-EA-OH was effective at 1 mg/kg IC in reducing myocardial damage whether administered prophylactically or therapeutically. In addition, rLip-EA-OH was effective at various dosages when administered intravenously at 15 minutes pre-occlusion (FIG. 7). These results indicate that rLip-EA-OH administration effectively decreases the damage to the heart due to ischemia-reperfusion injury.

Example 9

The rLip-EA-OH Enantiomer is More Effective than the Parent Moiety rLip-OH, the Racemic Mix r/sLip-EA-OH, and sLip-EA-OH Enantiomer for Reducing Myocardial Ischemia/Reperfusion (MI/R) Injury The rat model of myocardial ischemia-reperfusion (MI/R) injury described in Example 8 herein was employed to compare the efficacy of the pure rLip-EA-OH enantiomer with the efficacy of the parent moiety rLip-OH, pure sLip-EA-OH and the racemic mixture r/sLip-EA-OH in the treatment of MI/R injury.

Results:

A meta analysis of animals treated with either rLip-OH (2 mg/kg IC) or rLip-EA-OH (1 mg/kg IC) is shown in Table 7 as a % reduction compared to a saline vehicle control.

Ac-EA-OH, a non-lipoyl-containing compound, was also evaluated and found to be statistically similar to vehicle (data not shown). This result demonstrates that cardioprotection from IR injury following treatment with rLip-EA-OH was better than treatment with rLip-OH.

TABLE 7

An Efficacy Comparison of RLip-OH to RLip-EA-OH Examined in Rat Model of Myocardial Ischemia-Reperfusion Injury.

| Compound | Reduction of MI:AR Ratio Relative to Vehicle (%) |
|---|---|
| RLip-EA-OH | 31 ± 3* |
| RLip-OH | 19 ± 7# |

*Results based upon a meta analysis of RLip-EA-OH treated animals (n = 75) vs. vehicle-treated (n = 89) animals
Results based upon a meta analysis of RLip-OH treated animals (n = 18) vs. vehicle-treated (n = 19) animals An analysis of animals treated with either rLip-EA-OH (1 mg/kg IC) or r/sLip-EA-OH (1 mg/kg IC) is shown in Table 8 as a % reduction compared to a saline vehicle control. This result demonstrates that cardioprotection from IR injury following treatment with rLip-EA-OH was better than treatment with r/sLip-EA-OH.

TABLE 8

An Efficacy Comparison of RLip-EA-OH to R/SLip-EA-OH Examined in Rat Model of Myocardial Ischemia-Reperfusion Injury.

| Compound | Reduction of MI:AR Ratio Relative to Vehicle (%) |
|---|---|
| RLip-EA-OH | 31 ± 3* |
| R/SLip-EA-OH | 19 ± 5# |

*Results based upon a meta analysis of RLip-EA-OH treated animals (n = 75) vs. vehicle-treated (n = 89) animals
Results based upon a meta analysis of R/SLip-EA-OH treated animals (n = 26) vs. vehicle-treated (n = 25) animals The results of study comparing the single isomer compounds rLip-EA-OH and sLip-EA-OH is shown in Table 9. Compounds were administered at either 1 mg/kg or 2 mg/kg with a single bolus (IC) 15 minutes prior to the ischemic episode. A racemic mixture was prepared by adding equal amounts of rLip-EA-OH and sLip-EA-OH. Racemic r/sLip-EA-OH was also evaluated. Data is presented as the reduction of myocardial infarct (MI) size relative to the area at risk (AR). This result demonstrates that cardioprotection from IR injury following treatment with rLip-EA-OH was better than treatment with the corresponding sLip-EA-OH.

TABLE 9

Reduction of myocardial infarct (MI) size relative to the area at risk (AR) in Lip-EA-OH treated animals. Results based upon 9-10 animals/group.

| Compound | Treatment (mg/kg) | MI/AR | SEM |
|---|---|---|---|
| RLip-EA-OH | 2 | 0.290 | 0.038 |
| RLip-EA-OH + SLip-EA-OH | 1 + 1 | 0.331 | 0.035 |
| RLip-EA-OH | 1 | 0.337 | 0.02 |
| SLip-EA-OH | 2 | 0.400 | 0.042 |
| SLip-EA-OH | 1 | 0.401 | 0.026 |

REFERENCES

Alessi, D. R., Andjelkovic, M., Caudwell, B., Cron, P., Morrice, N., Cohen, P., Hemmings, B. A. Mechanism of activation of protein kinase B by insulin and IGF-1. EMBO J, 1996, 15, 6541-6551.

Alessi and Cohen, Curr. Opin. Genet. Dev. 8 (1998), 55-62.

Alessi et al., Curr. Biol. 8 (1998), 69-81.

Burger's Medicinal Chemistry and Drug Discovery, 5th Ed., Wolff, M. E., ed., New York: John Wiley, and Sons, Inc., 1995, 172-178, 949-982.

Bird T D, In: Harrison's Principles of Internal Medicine, 14th Ed., Fauci A S et al., eds, New York: McGraw-Hill, 1998, Chapter 26.

Buddhadeb, D., Takano, H., Tang, X.-L., et al., Role of Src protein tyrosine kinase in late preconditioning against myocardial infarction. Am J Physiol 2002, 283:H549.

Chan et al., Adv. Neurol., 71:271-279 (1996);

Chen, X., Zhang, X., Hubo, H., et al., $Ca^{2+}$ influx-induced sarcoplasmic reticulum $Ca^{2+}$ overload causes mitochondrial-dependent apoptosis in ventricular myocytes. Circ Res 2005, 97:1009.

Congi, F., et al., Presse. Med., 24: 1115-1118 (1995).

Datta, K., Bellacosa, A., Chan, T. O., Tsichlis, P. N. Akt is a direct target of the phosphatidylinositol 3-kinase: Activation by growth factors, v-src and vHa-ras, in Sf9 and mammalian cells. J Biol Chem 1996, 271: 30835.

Diesel, B., Kulhanek-Heinze, S., Holtje, M., et. al., α-Lipoic Acid as a directly binding activator of the insulin receptor: protection from hepatocyte apoptosis. Biochemistry, 2007 46:2146.

DiGuiseppi, J. and Fridovich, I., Crit. Rev. Toxicol., 12:315-342 (1984)

(Erdincler, D. S., et al., Clin. Chim. Acta, 265: 77-84 (1997).

Goodman and Gilman's The Pharmaceutical Basis of Therapeutics, McGraw-Hill, New York, N.Y.

Greene, T. W., Wuts, P. G. M., "Protective Groups in Organic Synthesis" John Wiley & Sons, Inc., New York, 1999.

(Halliwell, B. and Gutteridge, J. M. C., eds. (Oxford: Clarendon Press, 1989))

Hausenloy, D. J., Yellon, D. M. Reperfusion inury salvage kinase signaling: taking a RISK for cardioprotection. Heart Fail Rev 2007, 12:217.

Hausenloy, D. J., Yellon, D. M., New directions for protecting the heart against ischaemia-reperfusion injury: targeting the Reperfusion Injury Salvage Kinase (RISK)-pathway. Cardiovasc Res 2004, 61:448.

Joseph, S. K., Hajnoczky, G., IP3 receptors in cell survival and apoptosis: $Ca^{2+}$ release and beyond. Apoptosis 2007, 12:951.

Khan, M. T., Wagner, L. II, Yule, D. I., Bhanumathy, C., Joseph, S. K. 2006, Akt kinase phosphorylation of inositol 1,4,5-triphosphate receptors. J Biol Chem 281:3731.

Kulik, G., Klippel, A., Weber, M. J. Antiapoptotic signaling by the insulin-like growth factor I receptor, phosphatidylinositol 3-kinase and Akt. Mol Cell Biol 1997, 17:1595.

Lopes-Neblina, F., Toledo, A. H., Toledu-Pereyra, L. H. Molecular biology of apoptosis in ischemia and reperfusion. J Invest Surg 2005, 18:335.

Lucchesi, B. R., Am. J. Cardiol., 65:141-231 (1990).

Mecocci, P. et al., Free Radio. Biol. Med., 28: 1243-1248 (2000).

Matsui, T., Tao, J., del Monte, F., Lee, K.-H. et al, Aid Activation Preserves Cardiac Function and Prevents Injury After Transient Cardiac Ischemia In vivo, Circulation 2001, 104:330.

[Molecular Devices, FlexStation Application Note 2, Comparison of FLIPR® and FLEXstation™ for Calcium Mobilization Assays]

Moini, H., Tirosh, O., Park, Y. C., et al., R-α-Lipoic acid action on cell redox status, the insulin receptor and glucose uptake in 3T3-L1 adipocytes. *Arch Biochem Biophys* 2002, 397:384.

Otani, H., Ischemic preconditioning: From molecule mechanisms to therapeutic opportunities. *Antioxidants & Redox Signaling,* 2008, 10:207.

Packer, L., Witt, E. H., and Tritschler, H. J., Alpha-lipoic acid as a biological antioxidant. *Free Radic Biol Med* 1995, 19:227.

Pasdois, P., Quinlan, C. L., Rissa, A., et al., Ouabain protects rat hearts against ischemia-reperfusion injury via pathway involving Src kinase, mitoKATP, and ROS. *Am J Physiol* 2006, 292:H1470.

Pinton, P., Rizzuto, R., Bcl-2 and $Ca^{2+}$ homeostasis in the endoplasmic reticulum. *Cell Death Diff* 2006, 13:1409.

Piper, H. M., Abdallah, C., Schafer, C., The first minutes of reperfusion: a window of opportunity for cardioprotection. *Annals of Thoracic Surgery* 2003, 75:644.

Pulsinelli, W. A. et al., Ann. Neurol., 11: 499-502 (1982).

Raphael, J., Abedat, S., Rivo, J., et al., Volatile anesthetic preconditioning attenuates myocardial apoptosis in rabbits after regional ischemia and reperfusion via Akt signaling by modulation of Bcl-2 family proteins. *J Pharmacol Exp Ther* 2006, 318:186.

Ratanis, Pharmaceutical Executive, pp. 74-80 (April 1991).

Remington's Pharmaceutical Sciences, Mack Publishing Company, Easton, Pa.

Rosamond W, Flegal K, Furie K, et al., Heart disease and stroke statistics—2008 update: A report from the American Heart Association Statistics Committee and Stroke Statistics Subcommitte. *Circulation* 2008, 117:e25-e146.

Suzuki, Y. J., Growth factor signaling for cardioprotection against oxidative stress-induced apoptosis. *Antiox Redox Signal* 2003, 5:741.

Thomenius, M. J. and Distelhorst, C. W., Bcl-2 on the endoplasmic reticulum: protecting the mitochondria from a distance. *J Cell Sci* 2003, 116:4493.

U.S. Pat. No. 3,854,480 (issued to Zaffaroni).
U.S. Pat. No. 4,452,775 (issued to Kent).
U.S. Pat. No. 5,039,660 (issued to Leonard).
U.S. Pat. No. 5,990,092 (issued to Walsh).
U.S. Pat. No. 6,890,896.
US 2004/0122077.
US 2006/0241168.
US 2007/0219139

Vlahos C J, Matter W F, Hui K Y, Brown R F. A specific inhibitor of phosphatidylinositol 3-kinase, 2-(4-morpholinyl)-8-phenyl-4H-1-benzopyran-4-one (LY294002). *J Biol Chem* 1994, 269:5241-5248

Walton, M. et al., Brain Res. Rev., 29:137-168 (1999)

Yellon D. M., Hausenloy D. J., Myocardial reperfusion injury. *New England Journal of Medicine* 2007, 357:1121.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of activating at least one cytoprotective kinase in a cell, comprising contacting a cell with an effective amount of a compound represented by the following structural formula:

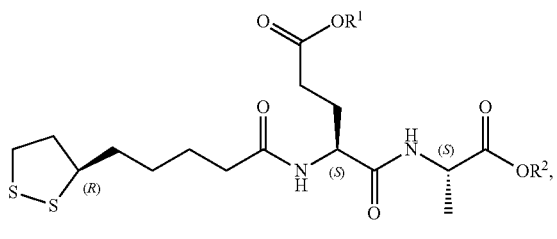

or a pharmaceutically acceptable salt thereof, wherein $R^1$ and $R^2$ in the compound are each independently H or a hydrolyzable group, and wherein the compound has a percent optical purity of at least 90% by weight relative to the other stereoisomers.

2. The method of claim 1, wherein the hydrolyzable group is selected from the group consisting of $(C_1-C_{10})$alkyl, $(C_2-C_{10})$alkenyl, $(C_2-C_{10})$alkynyl, $(C_1-C_{10})$alkoxy$(C_1-C_{10})$alkyl, $(C_1-C_{10})$alkoxy$(C_1-C_{10})$alkoxy$(C_1-C_{10})$alkyl, aryl and aryl$(C_1-C_{10})$alkyl, wherein each is optionally substituted with 1 to 3 substituents selected from the group consisting of halo, nitro, cyano, cyclopropyl, cyclobutyl, cyclopentyl, cyclohexyl, amino, $(C_1-C_6)$alkylamino, di$(C_1-C_6)$alkylamino, $(C_1-C_6)$alkyl, halo$(C_1-C_6)$alkyl, $(C_1-C_6)$alkoxy, halo$(C_1-C_6)$alkoxy, morpholino, phenyl, and benzyl.

3. The method of claim 1, wherein the hydrolyzable group is selected from the group consisting of methyl, ethyl, propyl, butyl, pentyl, hexyl, heptyl, allyl, ethoxymethyl, methoxyethyl, methoxyethoxymethyl, methoxyethoxyethyl, benzyl, pentafluorophenyl, 2-N-(morpholino)ethyl, dimethylaminoethyl and para-methoxybenzyl.

4. The method of claim 1, wherein the pharmaceutically acceptable salt comprises a monovalent cation or a divalent cation.

5. The method of claim 4, wherein the monovalent cation is a monovalent metal cation and the divalent cation is a divalent metal cation.

6. The method of claim 1, wherein the compound is represented by the following structural formula:

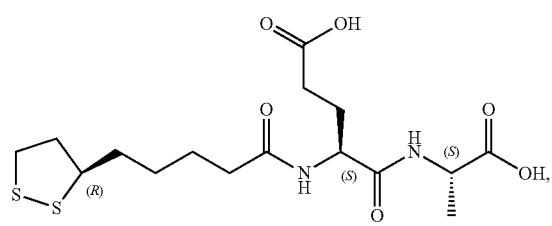

or a pharmaceutically acceptable salt thereof.

7. The method of claim 1, wherein the compound is represented by the following structural formula:

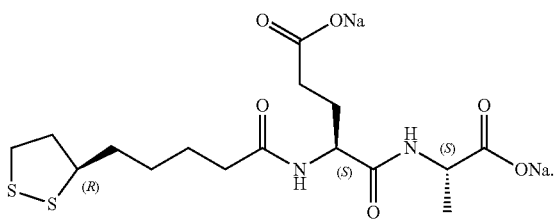

8. The method of claim 1, wherein the at least one cytoprotective kinase is selected from the group consisting of Akt kinase, IRK kinase, IGF1R kinase, and Src kinase.

9. The method of claim 1, wherein the compound has a percent optical purity by weight of at least 99%.

10. The method of claim 1, wherein the cell is in a subject.

11. The method of claim 10, wherein the subject is a human.

12. A method of inhibiting apoptosis in a subject in need thereof, comprising administering to the subject an effective amount of a compound represented by the following structural formula:

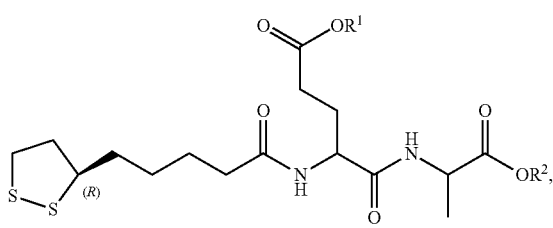

or a pharmaceutically acceptable salt thereof, wherein $R^1$ and $R^2$ in the compound are each independently H or a hydrolyzable group, and wherein the compound or pharmaceutically acceptable salt thereof is at least 90% enantiomerically pure.

13. A method of preventing cytosolic calcium overload in a subject in need thereof, comprising administering to the subject an effective amount of a compound represented by the following structural formula:

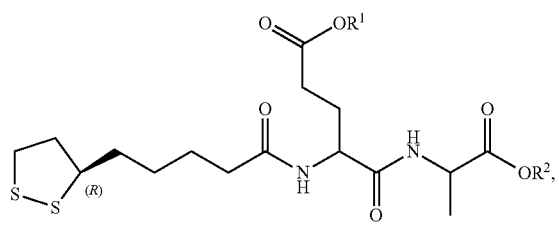

or a pharmaceutically acceptable salt thereof, wherein $R^1$ and $R^2$ in the compound are each independently H or a hydrolyzable group, and wherein the compound or pharmaceutically acceptable salt thereof is at least 90% enantiomerically pure.

14. A method of increasing peroxyl radical absorbance in a subject in need thereof, comprising administering to the subject an effective amount of a compound represented by the following structural formula:

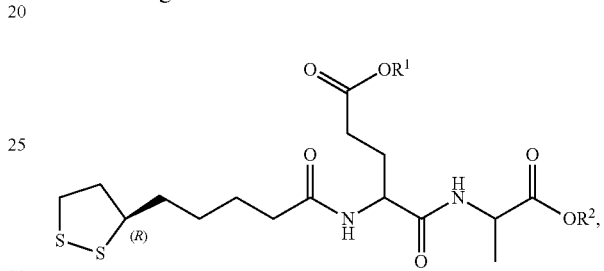

or a pharmaceutically acceptable salt thereof, wherein $R^1$ and $R^2$ in the compound are each independently H or a hydrolyzable group, and wherein the compound or pharmaceutically acceptable salt thereof is at least 90% enantiomerically pure.

* * * * *